United States Patent
Bertness

(10) Patent No.: US 7,446,536 B2
(45) Date of Patent: Nov. 4, 2008

(54) SCAN TOOL FOR ELECTRONIC BATTERY TESTER

(75) Inventor: Kevin I. Bertness, Batavia, IL (US)

(73) Assignee: Midtronics, Inc., Willowbrook, IL (US)

( * ) Notice: Subject to any disclaimer, the term of this patent is extended or adjusted under 35 U.S.C. 154(b) by 469 days.

(21) Appl. No.: 10/958,812

(22) Filed: Oct. 5, 2004

(65) Prior Publication Data

US 2005/0057256 A1    Mar. 17, 2005

Related U.S. Application Data

(63) Continuation-in-part of application No. 10/460,749, filed on Jun. 12, 2003, now Pat. No. 6,967,484, which is a continuation-in-part of application No. 10/280,186, filed on Oct. 25, 2002, now Pat. No. 6,759,849, which is a continuation-in-part of application No. 09/816,768, filed on Mar. 23, 2001, now Pat. No. 6,586,941.

(60) Provisional application No. 60/192,222, filed on Mar. 27, 2000.

(51) Int. Cl.
*G01N 27/416* (2006.01)
(52) U.S. Cl. .................................. 324/426
(58) Field of Classification Search ............... 320/132, 320/149; 324/426, 430, 433
See application file for complete search history.

(56) References Cited

U.S. PATENT DOCUMENTS

| | | | | |
|---|---|---|---|---|
| 2,000,665 A | 5/1935 | Neal | .................. | 439/440 |
| 2,417,940 A | 3/1947 | Lehman | .................. | 200/61.25 |
| 2,514,745 A | 7/1950 | Dalzell | .................. | 324/115 |
| 2,727,221 A | 12/1955 | Sprigg | .................. | 340/447 |
| 3,178,686 A | 4/1965 | Mills | .................. | 340/447 |
| 3,223,969 A | 12/1965 | Lawrence | .................. | 340/447 |
| 3,356,936 A | 12/1967 | Smith | .................. | 324/429 |
| 3,562,634 A | 2/1971 | Latner | .................. | 324/427 |
| 3,593,099 A | 7/1971 | Scholl | .................. | 320/127 |
| 3,607,673 A | 9/1971 | Seyl | .................. | 324/425 |
| 3,652,341 A | 3/1972 | Halsall et al. | .................. | 20/623.2 |
| 3,676,770 A | 7/1972 | Sharaf et al. | .................. | 324/430 |

(Continued)

FOREIGN PATENT DOCUMENTS

DE    29 26 716 B1    1/1981

(Continued)

OTHER PUBLICATIONS

"Electrochemical Impedance Spectroscopy in Battery Development and Testing", *Batteries International*, Apr. 1997, pp. 59 and 62-63.

(Continued)

*Primary Examiner*—Edward Tso
(74) *Attorney, Agent, or Firm*—Westman, Champlin & Kelly, P.A.

(57) ABSTRACT

A cable for connecting to an electronic battery tester, includes a first end configured to couple to a databus of a vehicle and a second end configured to couple to the electronic battery tester. An electrical connection extends between the first end and the second end and is configured to couple the electronic battery tester to the databus of the vehicle.

27 Claims, 7 Drawing Sheets

U.S. PATENT DOCUMENTS

| | | | |
|---|---|---|---|
| 3,729,989 A | 5/1973 | Little | 73/862.192 |
| 3,750,011 A | 7/1973 | Kreps | 324/430 |
| 3,753,094 A | 8/1973 | Furuishi et al. | 324/430 |
| 3,796,124 A | 3/1974 | Crosa | 411/521 |
| 3,808,522 A | 4/1974 | Sharaf | 324/430 |
| 3,811,089 A | 5/1974 | Strezelewicz | 324/170 |
| 3,873,911 A | 3/1975 | Champlin | 324/430 |
| 3,876,931 A | 4/1975 | Godshalk | 324/429 |
| 3,886,443 A | 5/1975 | Miyakawa et al. | 324/426 |
| 3,889,248 A | 6/1975 | Ritter | 340/636 |
| 3,906,329 A | 9/1975 | Bader | 320/134 |
| 3,909,708 A | 9/1975 | Champlin | 324/431 |
| 3,936,744 A | 2/1976 | Perlmutter | 324/772 |
| 3,946,299 A | 3/1976 | Christianson et al. | 320/430 |
| 3,947,757 A | 3/1976 | Grube et al. | 324/416 |
| 3,969,667 A | 7/1976 | McWilliams | 324/427 |
| 3,979,664 A | 9/1976 | Harris | 324/397 |
| 3,984,762 A | 10/1976 | Dowgiallo, Jr. | 324/430 |
| 3,984,768 A | 10/1976 | Staples | 324/712 |
| 3,989,544 A | 11/1976 | Santo | 429/65 |
| 4,008,619 A | 2/1977 | Alcaide et al. | 73/724 |
| 4,023,882 A | 5/1977 | Pettersson | 439/426 |
| 4,024,953 A | 5/1977 | Nailor, III | 206/344 |
| 4,047,091 A | 9/1977 | Hutchines et al. | 363/59 |
| 4,053,824 A | 10/1977 | Dupuis et al. | 324/434 |
| 4,056,764 A | 11/1977 | Endo et al. | 320/101 |
| 4,070,624 A | 1/1978 | Taylor | 324/772 |
| 4,086,531 A | 4/1978 | Bernier | 324/772 |
| 4,112,351 A | 9/1978 | Back et al. | 324/380 |
| 4,114,083 A | 9/1978 | Benham et al. | 320/150 |
| 4,126,874 A | 11/1978 | Suzuki et al. | 396/301 |
| 4,160,916 A | 7/1979 | Papasideris | 307/10.6 |
| 4,178,546 A | 12/1979 | Hulls et al. | 324/772 |
| 4,193,025 A | 3/1980 | Frailing et al. | 324/427 |
| 4,207,611 A | 6/1980 | Gordon | 324/503 |
| 4,217,645 A | 8/1980 | Barry et al. | 702/63 |
| 4,280,457 A | 7/1981 | Bloxham | 123/198 |
| 4,297,639 A | 10/1981 | Branham | 324/429 |
| 4,315,204 A | 2/1982 | Sievers et al. | 322/28 |
| 4,316,185 A | 2/1982 | Watrous et al. | 320/116 |
| 4,322,685 A | 3/1982 | Frailing et al. | 324/429 |
| 4,351,405 A | 9/1982 | Fields et al. | 180/65.2 |
| 4,352,067 A | 9/1982 | Ottone | 324/434 |
| 4,360,780 A | 11/1982 | Skutch, Jr. | 324/437 |
| 4,361,809 A | 11/1982 | Bil et al. | 324/426 |
| 4,363,407 A | 12/1982 | Buckler et al. | 209/3.3 |
| 4,369,407 A | 1/1983 | Korbell | 324/416 |
| 4,379,989 A | 4/1983 | Kurz et al. | 320/165 |
| 4,379,990 A | 4/1983 | Sievers et al. | 322/99 |
| 4,385,269 A | 5/1983 | Aspinwall et al. | 320/129 |
| 4,390,828 A | 6/1983 | Converse et al. | 320/153 |
| 4,392,101 A | 7/1983 | Saar et al. | 320/156 |
| 4,396,880 A | 8/1983 | Windebank | 320/156 |
| 4,408,157 A | 10/1983 | Beaubien | 324/712 |
| 4,412,169 A | 10/1983 | Dell'Orto | 320/123 |
| 4,423,378 A | 12/1983 | Marino et al. | 324/427 |
| 4,423,379 A | 12/1983 | Jacobs et al. | 324/429 |
| 4,424,491 A | 1/1984 | Bobbett et al. | 324/433 |
| 4,459,548 A | 7/1984 | Lentz et al. | 324/772 |
| 4,514,694 A | 4/1985 | Finger | 324/429 |
| 4,520,353 A | 5/1985 | McAuliffe | 340/636 |
| 4,564,798 A | 1/1986 | Young | 320/103 |
| 4,620,767 A | 11/1986 | Woolf | 439/217 |
| 4,633,418 A | 12/1986 | Bishop | 702/63 |
| 4,659,977 A | 4/1987 | Kissel et al. | 320/150 |
| 4,663,580 A | 5/1987 | Wortman | 320/153 |
| 4,665,370 A | 5/1987 | Holland | 324/429 |
| 4,667,143 A | 5/1987 | Cooper et al. | 320/153 |
| 4,667,279 A | 5/1987 | Maier | 363/46 |
| 4,678,998 A | 7/1987 | Muramatsu | 324/427 |
| 4,679,000 A | 7/1987 | Clark | 324/428 |
| 4,680,528 A | 7/1987 | Mikami et al. | 320/165 |
| 4,686,442 A | 8/1987 | Radomski | 320/123 |
| 4,697,134 A | 9/1987 | Burkum et al. | 320/134 |
| 4,707,795 A | 11/1987 | Alber et al. | 702/63 |
| 4,709,202 A | 11/1987 | Koenck et al. | 320/112 |
| 4,710,861 A | 12/1987 | Kanner | 363/46 |
| 4,719,428 A | 1/1988 | Liebermann | 324/436 |
| 4,723,656 A | 2/1988 | Kiernan et al. | 206/705 |
| 4,743,855 A | 5/1988 | Randin et al. | 324/430 |
| 4,745,349 A | 5/1988 | Palanisamy et al. | 320/125 |
| 4,773,011 A | 9/1988 | VanHoose | 701/30 |
| 4,816,768 A | 3/1989 | Champlin | 324/428 |
| 4,820,966 A | 4/1989 | Fridman | 320/116 |
| 4,825,170 A | 4/1989 | Champlin | 324/436 |
| 4,847,547 A | 7/1989 | Eng, Jr. et al. | 320/153 |
| 4,849,700 A | 7/1989 | Morioka et al. | 324/427 |
| 4,874,679 A | 10/1989 | Miyagawa | 429/91 |
| 4,876,495 A | 10/1989 | Palanisamy et al. | 320/106 |
| 4,881,038 A | 11/1989 | Champlin | 324/426 |
| 4,888,716 A | 12/1989 | Ueno | 702/63 |
| 4,912,416 A | 3/1990 | Champlin | 324/430 |
| 4,913,116 A | 4/1990 | Katogi et al. | 123/406.32 |
| 4,926,330 A | 5/1990 | Abe et al. | 364/424.03 |
| 4,929,931 A | 5/1990 | McCuen | 340/636 |
| 4,931,738 A | 6/1990 | MacIntyre et al. | 324/435 |
| 4,933,845 A | 6/1990 | Hayes | 710/104 |
| 4,934,957 A | 6/1990 | Bellusci | 439/504 |
| 4,937,528 A | 6/1990 | Palanisamy | 324/430 |
| 4,947,124 A | 8/1990 | Hauser | 324/430 |
| 4,949,046 A | 8/1990 | Seyfang | 324/427 |
| 4,956,597 A | 9/1990 | Heavey et al. | 320/129 |
| 4,968,941 A | 11/1990 | Rogers | 324/428 |
| 4,968,942 A | 11/1990 | Palanisamy | 324/430 |
| 5,004,979 A | 4/1991 | Marino et al. | 324/160 |
| 5,032,825 A | 7/1991 | Kuznicki | 340/636 |
| 5,037,778 A | 8/1991 | Stark et al. | 437/216 |
| 5,047,722 A | 9/1991 | Wurst et al. | 324/430 |
| 5,081,565 A | 1/1992 | Nabha et al. | 362/465 |
| 5,087,881 A | 2/1992 | Peacock | 324/378 |
| 5,095,223 A | 3/1992 | Thomas | 307/110 |
| 5,108,320 A | 4/1992 | Kimber | 439/883 |
| 5,109,213 A | 4/1992 | Williams | 340/447 |
| 5,126,675 A | 6/1992 | Yang | 324/435 |
| 5,140,269 A | 8/1992 | Champlin | 324/433 |
| 5,144,218 A | 9/1992 | Bosscha | 320/139 |
| 5,144,248 A | 9/1992 | Alexandres et al. | 324/428 |
| 5,159,272 A | 10/1992 | Rao et al. | 324/429 |
| 5,160,881 A | 11/1992 | Schramm et al. | 322/7 |
| 5,170,124 A | 12/1992 | Blair et al. | 324/434 |
| 5,179,335 A | 1/1993 | Nor | 320/159 |
| 5,194,799 A | 3/1993 | Tomantschger | 320/103 |
| 5,204,611 A | 4/1993 | Nor et al. | 320/145 |
| 5,214,370 A | 5/1993 | Harm et al. | 320/152 |
| 5,214,385 A | 5/1993 | Gabriel et al. | 324/434 |
| 5,241,275 A | 8/1993 | Fang | 324/430 |
| 5,254,952 A | 10/1993 | Salley et al. | 324/429 |
| 5,266,880 A | 11/1993 | Newland | 320/125 |
| 5,281,919 A | 1/1994 | Palanisamy | 324/427 |
| 5,281,920 A | 1/1994 | Wurst | 324/430 |
| 5,295,078 A | 3/1994 | Stich et al. | 320/136 |
| 5,298,797 A | 3/1994 | Redl | 327/387 |
| 5,300,874 A | 4/1994 | Shimamoto et al. | 320/106 |
| 5,302,902 A | 4/1994 | Groehl | 324/434 |
| 5,313,152 A | 5/1994 | Wozniak et al. | 320/118 |
| 5,315,287 A | 5/1994 | Sol | 340/455 |
| 5,321,626 A | 6/1994 | Palladino | 702/63 |
| 5,321,627 A | 6/1994 | Reher | 364/483 |
| 5,323,337 A | 6/1994 | Wilson et al. | 364/574 |
| 5,325,041 A | 6/1994 | Briggs | 320/149 |
| 5,331,268 A | 7/1994 | Patino et al. | 320/158 |
| 5,336,993 A | 8/1994 | Thomas et al. | 324/158.1 |
| 5,338,515 A | 8/1994 | Dalla Betta et al. | 422/95 |
| 5,339,018 A | 8/1994 | Brokaw | 320/147 |

| | | | | | | | |
|---|---|---|---|---|---|---|---|
| 5,343,380 | A | 8/1994 | Champlin ................... 363/46 | 5,710,503 | A | 1/1998 | Sideris et al. ............... 320/116 |
| 5,347,163 | A | 9/1994 | Yoshimura .................. 307/66 | 5,711,648 | A | 1/1998 | Hammerslag ............... 414/800 |
| 5,352,968 | A | 10/1994 | Reni et al. ................. 320/136 | 5,717,336 | A | 2/1998 | Basell et al. ................ 324/430 |
| 5,357,519 | A | 10/1994 | Martin et al. .............. 371/15.1 | 5,717,937 | A | 2/1998 | Fritz ......................... 320/128 |
| 5,365,160 | A | 11/1994 | Leppo et al. ............... 320/160 | 5,739,667 | A | 4/1998 | Matsuda et al. ............. 320/128 |
| 5,365,453 | A | 11/1994 | Startup et al. ............. 320/136 | 5,745,044 | A | 4/1998 | Hyatt, Jr. et al. ........... 340/5.23 |
| 5,369,364 | A | 11/1994 | Renirie et al. ............. 324/430 | 5,747,909 | A | 5/1998 | Syverson et al. ....... 310/156.56 |
| 5,381,096 | A | 1/1995 | Hirzel ....................... 324/427 | 5,747,967 | A | 5/1998 | Muljadi et al. .............. 320/148 |
| 5,402,007 | A | 3/1995 | Center et al. ............. 290/40 B | 5,754,417 | A | 5/1998 | Nicollini ...................... 363/60 |
| 5,410,754 | A | 4/1995 | Klotzbach et al. .......... 370/466 | 5,757,192 | A | 5/1998 | McShane et al. ............ 324/427 |
| 5,412,308 | A | 5/1995 | Brown ........................ 323/267 | 5,760,587 | A | 6/1998 | Harvey ....................... 324/434 |
| 5,412,323 | A | 5/1995 | Kato et al. .................. 324/429 | 5,772,468 | A | 6/1998 | Kowalski et al. ........... 439/506 |
| 5,425,041 | A | 6/1995 | Seko et al. ................ 372/45.01 | 5,773,978 | A | 6/1998 | Becker ....................... 324/430 |
| 5,426,371 | A | 6/1995 | Salley et al. ................ 324/429 | 5,778,326 | A | 7/1998 | Moroto et al. ................. 701/22 |
| 5,426,416 | A | 6/1995 | Jefferies et al. ............. 340/664 | 5,780,974 | A | 7/1998 | Pabla et al. ................... 315/82 |
| 5,432,025 | A | 7/1995 | Cox ........................... 429/65 | 5,780,980 | A | 7/1998 | Naito ......................... 318/139 |
| 5,432,426 | A | 7/1995 | Yoshida ..................... 320/160 | 5,789,899 | A | 8/1998 | van Phuoc et al. .......... 320/112 |
| 5,434,495 | A | 7/1995 | Toko ......................... 320/135 | 5,793,359 | A | 8/1998 | Ushikubo ................... 345/169 |
| 5,435,185 | A | 7/1995 | Eagan ......................... 73/587 | 5,796,239 | A | 8/1998 | van Phuoc et al. .......... 320/107 |
| 5,442,274 | A | 8/1995 | Tamai ........................ 320/146 | 5,808,469 | A | 9/1998 | Kopera ....................... 324/434 |
| 5,445,026 | A | 8/1995 | Eagan ......................... 73/591 | 5,818,234 | A | 10/1998 | McKinnon .................. 324/433 |
| 5,449,996 | A | 9/1995 | Matsumoto et al. ......... 320/148 | 5,821,756 | A | 10/1998 | McShane et al. ............ 324/430 |
| 5,449,997 | A | 9/1995 | Gilmore et al. ............. 320/148 | 5,821,757 | A | 10/1998 | Alvarez et al. .............. 324/434 |
| 5,451,881 | A | 9/1995 | Finger ........................ 324/433 | 5,825,174 | A | 10/1998 | Parker ........................ 324/106 |
| 5,453,027 | A | 9/1995 | Buell et al. .................. 439/433 | 5,831,435 | A | 11/1998 | Troy .......................... 324/426 |
| 5,457,377 | A | 10/1995 | Jonsson ............... 320/DIG. 21 | 5,832,396 | A | 11/1998 | Moroto et al. ................. 701/22 |
| 5,459,660 | A | 10/1995 | Berra .......................... 701/33 | 5,850,113 | A | 12/1998 | Weimer et al. .............. 307/125 |
| 5,469,043 | A | 11/1995 | Cherng et al. ............... 320/161 | 5,862,515 | A | 1/1999 | Kobayashi et al. ............ 702/63 |
| 5,485,090 | A | 1/1996 | Stephens .................... 324/433 | 5,865,638 | A | 2/1999 | Trafton ....................... 439/288 |
| 5,488,300 | A | 1/1996 | Jamieson .................... 324/432 | 5,871,858 | A | 2/1999 | Thomsen et al. ............... 429/7 |
| 5,508,599 | A | 4/1996 | Koench ...................... 320/138 | 5,872,443 | A | 2/1999 | Williamson ................. 320/160 |
| 5,519,383 | A | 5/1996 | De La Rosa ................ 340/636 | 5,872,453 | A | 2/1999 | Shimoyama et al. ........ 324/431 |
| 5,528,148 | A | 6/1996 | Rogers ....................... 320/137 | 5,883,306 | A | 3/1999 | Hwang ....................... 73/146.8 |
| 5,537,967 | A | 7/1996 | Tashiro et al. ............. 123/192.1 | 5,895,440 | A | 4/1999 | Proctor et al. ................. 702/63 |
| 5,541,489 | A | 7/1996 | Dunstan ..................... 320/134 | 5,912,534 | A | 6/1999 | Benedict ..................... 315/82 |
| 5,546,317 | A | 8/1996 | Andrieu ....................... 702/63 | 5,914,605 | A | 6/1999 | Bertness ..................... 324/430 |
| 5,548,273 | A | 8/1996 | Nicol et al. ................. 340/434 | 5,927,938 | A | 7/1999 | Hammerslag ............... 414/809 |
| 5,550,485 | A | 8/1996 | Falk ........................... 324/772 | 5,929,609 | A | 7/1999 | Joy et al. ...................... 322/25 |
| 5,561,380 | A | 10/1996 | Sway-Tin et al. ............ 324/509 | 5,939,855 | A | 8/1999 | Proctor et al. ............... 320/104 |
| 5,562,501 | A | 10/1996 | Kinoshita et al. ............ 439/852 | 5,939,861 | A | 8/1999 | Joko et al. ................... 320/122 |
| 5,563,496 | A | 10/1996 | McClure ..................... 320/128 | 5,945,829 | A | 8/1999 | Bertness ..................... 324/430 |
| 5,572,136 | A | 11/1996 | Champlin ................... 324/426 | 5,946,605 | A | 8/1999 | Takahisa et al. .............. 455/68 |
| 5,573,611 | A | 11/1996 | Koch et al. ................ 152/152.1 | 5,951,229 | A | 9/1999 | Hammerslag ............... 414/398 |
| 5,574,355 | A | 11/1996 | McShane et al. ............ 320/161 | 5,961,561 | A | 10/1999 | Wakefield, II ................ 701/29 |
| 5,578,915 | A | 11/1996 | Crouch, Jr. et al. .......... 324/428 | 5,961,604 | A | 10/1999 | Anderson et al. ............ 709/229 |
| 5,583,416 | A | 12/1996 | Klang ........................ 320/160 | 5,969,625 | A | 10/1999 | Russo ..................... 340/636.19 |
| 5,585,416 | A | 12/1996 | Audett et al. ................. 522/35 | 5,978,805 | A | 11/1999 | Carson ......................... 707/10 |
| 5,585,728 | A | 12/1996 | Champlin ................... 324/427 | 5,982,138 | A | 11/1999 | Krieger ...................... 320/105 |
| 5,589,757 | A | 12/1996 | Klang ........................ 320/160 | 6,002,238 | A | 12/1999 | Champlin ................... 320/134 |
| 5,592,093 | A | 1/1997 | Klingbiel .................... 324/426 | 6,005,759 | A | 12/1999 | Hart et al. ..................... 361/66 |
| 5,592,094 | A | 1/1997 | Ichikawa .................... 324/427 | 6,008,652 | A | 12/1999 | Theofanopoulos et al. .. 324/434 |
| 5,596,260 | A | 1/1997 | Moravec et al. ............. 320/135 | 6,009,369 | A | 12/1999 | Boisvert et al. ............... 701/99 |
| 5,598,098 | A | 1/1997 | Champlin ................... 324/430 | 6,016,047 | A | 1/2000 | Notten et al. ................ 320/137 |
| 5,602,462 | A | 2/1997 | Stich et al. .................. 323/258 | 6,031,354 | A | 2/2000 | Wiley et al. ................. 320/116 |
| 5,606,242 | A | 2/1997 | Hull et al. ................... 320/106 | 6,031,368 | A | 2/2000 | Klippel et al. .............. 324/133 |
| 5,614,788 | A | 3/1997 | Mullins et al. ................ 315/82 | 6,037,745 | A | 3/2000 | Koike et al. ................. 320/104 |
| 5,621,298 | A | 4/1997 | Harvey ....................... 320/134 | 6,037,751 | A | 3/2000 | Klang ........................ 320/160 |
| 5,633,985 | A | 5/1997 | Severson et al. ............ 704/267 | 6,037,777 | A | 3/2000 | Champlin ................... 324/430 |
| 5,637,978 | A | 6/1997 | Kellett et al. ................ 320/104 | 6,037,778 | A | 3/2000 | Makhija ...................... 324/433 |
| 5,642,031 | A | 6/1997 | Brotto ........................ 320/152 | 6,046,514 | A | 4/2000 | Rouillard et al. .............. 307/77 |
| 5,650,937 | A | 7/1997 | Bounaga ....................... 702/6 | 6,051,976 | A | 4/2000 | Bertness ..................... 324/426 |
| 5,652,501 | A | 7/1997 | McClure et al. ............. 320/118 | 6,055,468 | A | 4/2000 | Kaman et al. ................. 701/29 |
| 5,653,659 | A | 8/1997 | Kunibe et al. ............... 477/111 | 6,061,638 | A | 5/2000 | Joyce .......................... 702/63 |
| 5,654,623 | A | 8/1997 | Shiga et al. ................. 320/106 | 6,064,372 | A | 5/2000 | Kahkoska ................... 345/173 |
| 5,656,920 | A | 8/1997 | Cherng et al. ............... 320/161 | 6,072,299 | A | 6/2000 | Kurle et al. ................. 320/112 |
| 5,661,368 | A | 8/1997 | Deol et al. .................... 315/82 | 6,072,300 | A | 6/2000 | Tsuji .......................... 320/116 |
| 5,675,234 | A | 10/1997 | Greene ................. 320/DIG. 18 | 6,081,098 | A | 6/2000 | Bertness et al. ............. 320/134 |
| 5,677,077 | A | 10/1997 | Faulk .......................... 429/90 | 6,081,109 | A | 6/2000 | Seymour et al. ............ 324/127 |
| 5,684,678 | A | 11/1997 | Barrett ......................... 363/17 | 6,091,238 | A | 7/2000 | McDermott ............... 324/207.2 |
| 5,699,050 | A | 12/1997 | Kanazawa .................. 340/636 | 6,091,245 | A | 7/2000 | Bertness ..................... 324/426 |
| 5,701,089 | A | 12/1997 | Perkins ...................... 324/772 | 6,094,033 | A | 7/2000 | Ding et al. .................. 320/132 |
| 5,705,929 | A | 1/1998 | Caravello et al. ............ 324/430 | 6,100,670 | A | 8/2000 | Levesque .................... 320/150 |
| 5,707,015 | A | 1/1998 | Guthrie ...................... 241/120 | 6,104,167 | A | 8/2000 | Bertness et al. ............. 320/132 |

| | | | | | | |
|---|---|---|---|---|---|---|
| 6,114,834 A | 9/2000 | Parise | 320/109 | 6,497,209 B1 | 12/2002 | Karuppanan et al. | 123/179.3 |
| 6,137,269 A | 10/2000 | Champlin | 320/150 | 6,505,507 B1 | 1/2003 | Imao et al. | 73/146.5 |
| 6,140,797 A | 10/2000 | Dunn | 320/105 | 6,507,196 B2 | 1/2003 | Thomsen et al. | 324/436 |
| 6,144,185 A | 11/2000 | Dougherty et al. | 320/132 | 6,526,361 B1 | 2/2003 | Jones et al. | 702/63 |
| 6,150,793 A | 11/2000 | Lesesky et al. | 320/104 | 6,529,723 B1 | 3/2003 | Bentley | 455/405 |
| 6,158,000 A | 12/2000 | Collins | 713/1 | 6,531,848 B1 | 3/2003 | Chitsazan et al. | 320/153 |
| 6,161,640 A | 12/2000 | Yamaguchi | 180/65.8 | 6,534,993 B2 | 3/2003 | Bertness | 324/433 |
| 6,163,156 A | 12/2000 | Bertness | 324/426 | 6,544,078 B2 | 4/2003 | Palmisano et al. | 439/762 |
| 6,164,063 A | 12/2000 | Mendler | 60/274 | 6,545,599 B2 | 4/2003 | Derbyshire et al. | 340/442 |
| 6,167,349 A | 12/2000 | Alvarez | 702/63 | 6,556,019 B2 | 4/2003 | Bertness | 324/426 |
| 6,172,483 B1 | 1/2001 | Champlin | 320/134 | 6,566,883 B1 | 5/2003 | Vonderhaar et al. | 324/426 |
| 6,172,505 B1 | 1/2001 | Bertness | 324/430 | 6,570,385 B1 | 5/2003 | Roberts et al. | 324/378 |
| 6,177,737 B1 | 1/2001 | Palfey et al. | 307/64 | 6,586,941 B2 | 7/2003 | Bertness et al. | 324/426 |
| 6,181,545 B1 | 1/2001 | Amatucci et al. | 361/502 | 6,597,150 B1 | 7/2003 | Bertness et al. | 320/104 |
| 6,211,651 B1 | 4/2001 | Nemoto | 320/133 | 6,600,815 B1 | 7/2003 | Walding | 379/93.07 |
| 6,215,275 B1 | 4/2001 | Bean | 320/106 | 6,611,740 B2 | 8/2003 | Lowrey et al. | 701/29 |
| 6,218,936 B1 | 4/2001 | Imao | 340/447 | 6,618,644 B2 | 9/2003 | Bean | 700/231 |
| 6,222,342 B1 | 4/2001 | Eggert et al. | 320/105 | 6,621,272 B2 | 9/2003 | Champlin | 324/426 |
| 6,222,369 B1 | 4/2001 | Champlin | 324/430 | 6,623,314 B1 | 9/2003 | Cox et al. | 439/759 |
| D442,503 S | 5/2001 | Lundbeck et al. | D10/77 | 6,628,011 B2 | 9/2003 | Droppo et al. | 307/43 |
| 6,225,808 B1 | 5/2001 | Varghese et al. | 324/426 | 6,629,054 B2 | 9/2003 | Makhija et al. | 702/113 |
| 6,236,332 B1 | 5/2001 | Conkright et al. | 340/3.1 | 6,633,165 B2 | 10/2003 | Bertness | 324/426 |
| 6,238,253 B1 | 5/2001 | Qualls | 439/759 | 6,635,974 B1 | 10/2003 | Karuppana et al. | 307/140 |
| 6,242,887 B1 | 6/2001 | Burke | 320/104 | 6,667,624 B1 | 12/2003 | Raichle et al. | 324/522 |
| 6,249,124 B1 | 6/2001 | Bertness | 324/426 | 6,679,212 B2 | 1/2004 | Kelling | 123/179.28 |
| 6,250,973 B1 | 6/2001 | Lowery et al. | 439/763 | 6,696,819 B2 | 2/2004 | Bertness | 320/134 |
| 6,254,438 B1 | 7/2001 | Gaunt | 439/755 | 6,707,303 B2 | 3/2004 | Bertness et al. | 324/426 |
| 6,259,170 B1 | 7/2001 | Limoge et al. | 307/10.8 | 6,736,941 B2 | 5/2004 | Oku et al. | 203/68 |
| 6,259,254 B1 | 7/2001 | Klang | 324/427 | 6,737,831 B2 | 5/2004 | Champlin | 320/132 |
| 6,262,563 B1 | 7/2001 | Champlin | 320/134 | 6,738,697 B2 | 5/2004 | Breed | 701/29 |
| 6,263,268 B1 | 7/2001 | Nathanson | 701/29 | 6,744,149 B1 | 6/2004 | Karuppana et al. | 307/31 |
| 6,271,643 B1 | 8/2001 | Becker et al. | 320/112 | 6,745,153 B2 | 6/2004 | White et al. | 702/184 |
| 6,271,748 B1 | 8/2001 | Derbyshire et al. | 340/442 | 6,759,849 B2 | 7/2004 | Bertness | 324/426 |
| 6,275,008 B1 | 8/2001 | Arai et al. | 320/132 | 6,777,945 B2 | 8/2004 | Roberts et al. | 324/426 |
| 6,294,896 B1 | 9/2001 | Champlin | 320/134 | 6,781,382 B2 | 8/2004 | Johnson | 324/426 |
| 6,294,897 B1 | 9/2001 | Champlin | 320/153 | 6,788,025 B2 | 9/2004 | Bertness et al. | 320/104 |
| 6,304,087 B1 | 10/2001 | Bertness | 324/426 | 6,795,782 B2 | 9/2004 | Bertness et al. | 702/63 |
| 6,307,349 B1 | 10/2001 | Koenck et al. | 320/112 | 6,805,090 B2 | 10/2004 | Bertness et al. | 123/198 |
| 6,310,481 B2 | 10/2001 | Bertess | 324/430 | 6,806,716 B2 | 10/2004 | Bertness et al. | 324/426 |
| 6,313,607 B1 | 11/2001 | Champlin | 320/132 | 6,933,727 B2 | 8/2005 | Bertness et al. | 324/426 |
| 6,313,608 B1 | 11/2001 | Varghese et al. | 32/132 | 6,967,484 B2 | 11/2005 | Bertness | 324/426 |
| 6,316,914 B1 | 11/2001 | Bertness | 320/134 | 6,998,847 B2 | 2/2006 | Bertness et al. | 324/426 |
| 6,320,351 B1 | 11/2001 | Ng et al. | 320/104 | 7,003,410 B2 | 2/2006 | Bertness et al. | 702/63 |
| 6,323,650 B1 | 11/2001 | Bertness et al. | 324/426 | 7,003,411 B2 | 2/2006 | Bertness | 702/63 |
| 6,329,793 B1 | 12/2001 | Bertness et al. | 320/132 | 7,012,433 B2 | 3/2006 | Smith et al. | 324/426 |
| 6,331,762 B1 | 12/2001 | Bertness | 320/134 | 7,058,525 B2 | 6/2006 | Bertness et al. | 702/63 |
| 6,332,113 B1 | 12/2001 | Bertness | 702/63 | 7,081,755 B2 | 7/2006 | Klang et al. | 324/426 |
| 6,346,795 B2 | 2/2002 | Haraguchi et al. | 320/136 | 7,106,070 B2 | 9/2006 | Bertness et al. | 324/538 |
| 6,347,958 B1 | 2/2002 | Tsai | 439/488 | 7,116,109 B2 | 10/2006 | Klang | 324/426 |
| 6,351,102 B1 | 2/2002 | Troy | 320/139 | 7,126,341 B2 | 10/2006 | Bertness et al. | 324/426 |
| 6,356,042 B1 | 3/2002 | Kahlon et al. | 318/138 | 2002/0004694 A1 | 1/2002 | McLeod et al. | 701/29 |
| 6,359,441 B1 | 3/2002 | Bertness | 324/426 | 2002/0010558 A1 | 1/2002 | Bertness et al. | 702/63 |
| 6,359,442 B1 | 3/2002 | Henningson et al. | 324/426 | 2002/0030495 A1 | 3/2002 | Kechmire | 324/427 |
| 6,363,303 B1 | 3/2002 | Bertness | 701/29 | 2002/0041175 A1 | 4/2002 | Lauper et al. | 320/106 |
| RE37,677 E | 4/2002 | Irie | 315/83 | 2002/0044050 A1 | 4/2002 | Derbyshire et al. | 340/442 |
| 6,377,031 B1 | 4/2002 | Karuppana et al. | 323/220 | 2002/0050163 A1 | 5/2002 | Makhija et al. | 73/116 |
| 6,384,608 B1 | 5/2002 | Namaky | 324/430 | 2002/0171428 A1 | 11/2002 | Bertness | 324/426 |
| 6,388,448 B1 | 5/2002 | Cervas | 324/426 | 2002/0176010 A1 | 11/2002 | Wallach et al. | 348/362 |
| 6,392,414 B2 | 5/2002 | Bertness | 324/429 | 2003/0009270 A1 | 1/2003 | Breed | 701/29 |
| 6,396,278 B1 | 5/2002 | Makhija | 324/402 | 2003/0025481 A1 | 2/2003 | Bertness | 324/427 |
| 6,411,098 B1 | 6/2002 | Laletin | 324/436 | 2003/0036909 A1 | 2/2003 | Kato | 704/275 |
| 6,417,669 B1 | 7/2002 | Champlin | 324/426 | 2003/0088375 A1 | 5/2003 | Bertness et al. | 702/63 |
| 6,424,157 B1 | 7/2002 | Gollomp et al. | 324/430 | 2003/0184262 A1 | 10/2003 | Makhija | 320/130 |
| 6,424,158 B2 | 7/2002 | Klang | 324/433 | 2003/0184306 A1 | 10/2003 | Bertness et al. | 324/426 |
| 6,437,957 B1 | 8/2002 | Karuppana et al. | 361/78 | 2003/0187556 A1 | 10/2003 | Suzuki | 701/29 |
| 6,441,585 B1 | 8/2002 | Bertness | 320/132 | 2003/0194672 A1 | 10/2003 | Roberts et al. | 431/196 |
| 6,445,158 B1 | 9/2002 | Bertness et al. | 320/104 | 2003/0214395 A1 | 11/2003 | Flowerday et al. | 340/445 |
| 6,449,726 B1 | 9/2002 | Smith | 713/340 | 2004/0000590 A1 | 1/2004 | Raichle et al. | 235/462.01 |
| 6,456,045 B1 | 9/2002 | Troy et al. | 320/139 | 2004/0000891 A1 | 1/2004 | Raichle et al. | 320/107 |
| 6,465,908 B1 | 10/2002 | Karuppana et al. | 307/31 | 2004/0000893 A1 | 1/2004 | Raichle et al. | 320/135 |
| 6,466,025 B1 | 10/2002 | Klang | 324/429 | 2004/0000913 A1 | 1/2004 | Raichle et al. | 324/426 |
| 6,466,026 B1 | 10/2002 | Champlin | 324/430 | 2004/0000915 A1 | 1/2004 | Raichle et al. | 324/522 |
| 6,495,990 B2 | 12/2002 | Champlin | 320/132 | 2004/0002824 A1 | 1/2004 | Raichle et al. | 702/63 |

| | | | | |
|---|---|---|---|---|
| 2004/0002825 A1 | 1/2004 | Raichle et al. | | 702/63 |
| 2004/0002836 A1 | 1/2004 | Raichle et al. | | 702/188 |
| 2004/0044452 A1 | 3/2004 | Bauer et al. | | 701/33 |
| 2004/0049361 A1 | 3/2004 | Hamdan et al. | | 702/115 |
| 2004/0051533 A1 | 3/2004 | Namaky | | 324/426 |
| 2004/0054503 A1 | 3/2004 | Namaky | | 702/183 |
| 2004/0227523 A1* | 11/2004 | Namaky | | 324/537 |
| 2004/0239332 A1 | 12/2004 | Mackel et al. | | 324/426 |
| 2005/0017726 A1* | 1/2005 | Koran et al. | | 324/433 |
| 2005/0043868 A1 | 2/2005 | Mitcham | | 701/29 |
| 2005/0057256 A1 | 3/2005 | Bertness | | 324/426 |
| 2005/0102073 A1 | 5/2005 | Ingram | | 701/29 |
| 2005/0182536 A1 | 8/2005 | Doyle et al. | | 701/29 |
| 2005/0256617 A1 | 11/2005 | Cawthorne et al. | | 701/22 |
| 2006/0030980 A1 | 2/2006 | St. Denis | | 701/29 |
| 2006/0089767 A1 | 4/2006 | Sowa | | 701/29 |
| 2006/0217914 A1 | 9/2006 | Bertness | | 702/113 |

FOREIGN PATENT DOCUMENTS

| | | |
|---|---|---|
| EP | 0 022 450 A1 | 1/1981 |
| EP | 0 637 754 A1 | 2/1995 |
| EP | 0 772 056 A1 | 5/1997 |
| EP | 0 982 159 A2 | 3/2000 |
| EP | 0982159 | 3/2000 |
| FR | 2 749 397 | 12/1997 |
| GB | 2 029 586 | 3/1980 |
| GB | 2 088 159 A | 6/1982 |
| GB | 2 246 916 A | 10/1990 |
| GB | 2 387 235 A | 10/2003 |
| JP | 59-17892 | 1/1984 |
| JP | 59-17893 | 1/1984 |
| JP | 59-17894 | 1/1984 |
| JP | 59017894 | 1/1984 |
| JP | 59215674 | 12/1984 |
| JP | 60225078 | 11/1985 |
| JP | 62-180284 | 8/1987 |
| JP | 63027776 | 2/1988 |
| JP | 03274479 | 12/1991 |
| JP | 03282276 | 12/1991 |
| JP | 4-8636 | 1/1992 |
| JP | 04095788 | 3/1992 |
| JP | 04131779 | 5/1992 |
| JP | 04372536 | 12/1992 |
| JP | 5216550 | 8/1993 |
| JP | 7-128414 | 5/1995 |
| JP | 09061505 | 3/1997 |
| JP | 10056744 | 2/1998 |
| JP | 10232273 | 9/1998 |
| JP | 11103503 A | 4/1999 |
| RU | 2089015 C1 | 8/1997 |
| WO | WO 93/22666 | 11/1993 |
| WO | WO 94/05069 | 3/1994 |
| WO | WO 96/06747 | 3/1996 |
| WO | WO 97/44652 | 11/1997 |
| WO | WO 98/04910 | 2/1998 |
| WO | WO 98/58270 | 12/1998 |
| WO | WO 99/23738 | 5/1999 |
| WO | WO 00/16083 | 3/2000 |
| WO | WO 00/62049 | 10/2000 |
| WO | WO 00/67359 | 11/2000 |
| WO | WO 01/59443 | 2/2001 |
| WO | WO 00/16614 A1 | 3/2001 |
| WO | WO 00/16615 A1 | 3/2001 |
| WO | WO 01/51947 | 7/2001 |

OTHER PUBLICATIONS

"Battery Impedance", by E. Willihnganz et al., *Electrical Engineering*, Sep. 1959, pp. 922-925.

"Determining The End of Battery Life", by S. DeBardelaben, *IEEE*, 1986, pp. 365-368.

"A Look at the Impedance of a Cell", by S. Debardelaben, *IEEE*, 1988, pp. 394-397.

"The Impedance of Electrical Storage Cells", by N.A. Hampson et al., *Journal of Applied Electrochemistry*, 1980, pp. 3-11.

"A Package for Impedance/Admittance Data Analysis", by B. Boukamp, *Solid State Ionics*, 1986, pp. 136-140.

"Precision of Impedance Spectroscopy Estimates of Bulk, Reaction Rate, and Diffusion Parameters", by J. Macdonald et al., *J. Electroanal, Chem.*, 1991, pp. 1-11.

Internal Resistance: Harbinger of Capacity Loss in Starved Electrolyte Sealed Lead Acid Batteries, by Vaccaro, F.J. et al., *AT&T Bell Laboratories*, 1987 IEEE, Ch. 2477, pp. 128,131.

IEEE Recommended Practice For Maintenance, Testings, and Replacement of Large Lead Storage Batteries for Generating Stations and Substations, *The Institute of Electrical and Electronics Engineers, Inc., ANSI/IEEE Std.* 450-1987, Mar. 9, 1987, pp. 7-15.

"Field and Laboratory Studies to Assess the State of Health of Valve-Regulated Lead Acid Batteries: Part I Conductance/Capacity Correlation Studies", by D. Feder et al., *IEEE*, Aug. 1992, pp. 218-233.

"JIS Japanese Industrial Standard-Lead Acid Batteries for Automobiles", *Japanese Standards Association UDC*, 621.355.2:629.113.006, Nov. 1995.

"Performance of Dry Cells", by C. Hambuechen, Preprint of *Am. Electrochem. Soc.*, Apr. 18-20, 1912, paper No. 19, pp. 1-5.

"A Bridge for Measuring Storage Battery Resistance", by E. Willihncanz, *The Electrochemical Society*, preprint 79-20, Apr. 1941, pp. 253-258.

National Semiconductor Corporation, "High Q Notch Filter", 3/69, Linear Brief 5, Mar. 1969.

Burr-Brown Corporation, "Design A 60 Hz Notch Filter with the UAF42", 1/94, AB-071, 1994.

National Semiconductor Corporation, "LMF90-4th-Order Elliptic Notch Filter", 12/94, RRD-B30M115, Dec. 1994.

"Alligator Clips with Wire Penetrators" *J.S. Popper, Inc.* product information, downloaded from http://www.jspopper.com/, undated.

"#12: LM78S40 Simple Switcher DC to DC Converter", *ITM e-Catalog*, downloaded from http://www.pcbcafe.com, undated.

"Simple DC-DC Converts Allows Use of Single Battery", *Electronix Express*, downloaded from http://www.elexp.com/t_dc-dc.htm, undated.

"DC-DC Converter Basics", *Power Designers*, downloaded from http://www.powederdesigners.com/InforWeb.design_center/articles/DC-DC/converter.shtm, undated.

"Notification of Transmittal of The International Search Report or the Declaration", PCT/US02/29461.

"Notification of Transmittal of The International Search Report or the Declaration", PCT/US03/07546.

"Notification of Transmittal of The International Search Report or the Declaration", PCT/US03/06577.

"Notification of Transmittal of The International Search Report or the Declaration", PCT/US03/07837.

"Notification of Transmittal of The International Search Report or the Declaration", PCT/US03/41561.

"Notification of Transmittal of The International Search Report or the Declaration", PCT/US03/27696.

"Programming Training Course, 62-000 Series Smart Engine Analyzer", Testproducts Division, Kalamazoo, Michigan, pp. 1-207, (1984).

"Operators Manual, Modular Computer Analyzer Model MCA 3000", Sun Electric Corporation, Crystal Lake, Illinois, pp. 1-1-14-13, (1991).

Notification of Transmitatl of the International Search Report for PCT/US03/30707.

"Dynamic modelling of lead/acid batteries using impedance spectroscopy for parameter identification", Journal of Power Sources, pp. 69-84, (1997).

"A review of impedance measurements for determination of the state-of-charge or state-of-health of secondary batteries", Journal of Power Sources, pp. 59-69, (1998).

"Improved Impedance Spectroscopy Technique For Status Determination of Production $Li/SO_2$ Batteries" Terrill Atwater et al., pp. 10-113, (1992).

"Search Report Under Section 17" for Great Britain Application No. GB0421447.4. (Jan. 28, 2005).

"Results of Discrete Frequency Immittance Spectroscopy (DFIS) Measurements of Lead Acid Batteries", by K.S. Champlin et al., *Proceedings of 23rd International Teleco Conference* (*INTELEC*), published Oct. 2001, IEE, pp. 433-440.

"Examination Report" from the U.K. Patent Office for U.K. App. No. 0417678.0.

"Office Action" from related U.S. Appl. No. 11/352,945.

* cited by examiner

SCAN TOOL FOR ELECTRONIC BATTERY TESTER

The present application is a Continuation-In-Part of U.S. Ser. No. 10/460,749, filed Jun. 12, 2003, now U.S. Pat. No. 6,967,484 which is a Continuation-In-Part of U.S. Ser. No. 10/280,186, filed Oct. 25, 2002, now U.S. Pat. No. 6,759,849, which is a Continuation-In-Part of U.S. patent application Ser. No. 09/816,768, filed Mar. 23, 2001, now U.S. Pat No. 6,586,941, which claims the benefit of U.S. provisional patent application Ser. No. 60/192,222, filed Mar. 27, 2000, the contents of which are hereby incorporated by reference in their entirety.

BACKGROUND OF THE INVENTION

The present invention relates to battery testers of the type used to test storage batteries. More specifically, the present invention relates to a modular battery tester capable of interfacing with other types of test equipment.

Various types of battery testers are known in the art. One type of battery tester is based upon the measurement of a dynamic parameter, such as dynamic conductance. Examples of various battery testers and monitors are forth in U.S. Pat. No. 3,873,911, issued Mar. 25, 1975, to Champlin, entitled ELECTRONIC BATTERY TESTING DEVICE; U.S. Pat. No. 3,909,708, issued Sep. 30, 1975, to Champlin, entitled ELECTRONIC BATTERY TESTING DEVICE; U.S. Pat. No. 4,816,768, issued Mar. 28, 1989, to Champlin, entitled ELECTRONIC BATTERY TESTING DEVICE; U.S. Pat. No. 4,825,170, issued Apr. 25, 1989, to Champlin, entitled ELECTRONIC BATTERY TESTING DEVICE WITH AUTOMATIC VOLTAGE SCALING; U.S. Pat. No. 4,881,038, issued Nov. 14, 1989, to Champlin, entitled ELECTRONIC BATTERY TESTING DEVICE WITH AUTOMATIC VOLTAGE SCALING TO DETERMINE DYNAMIC CONDUCTANCE; U.S. Pat. No. 4,912,416, issued Mar. 27, 1990, to Champlin, entitled ELECTRONIC BATTERY TESTING DEVICE WITH STATE-OF-CHARGE COMPENSATION; U.S. Pat. No. 5,140,269, issued Aug. 18, 1992, to Champlin, entitled ELECTRONIC TESTER FOR ASSESSING BATTERY/CELL CAPACITY; U.S. Pat. No. 5,343,380, issued Aug. 30, 1994, entitled METHOD AND APPARATUS FOR SUPPRESSING TIME-VARYING SIGNALS IN BATTERIES UNDERGOING CHARGING OR DISCHARGING; U.S. Pat. No. 5,572,136, issued Nov. 5, 1996, entitled ELECTRONIC BATTERY TESTER DEVICE; U.S. Pat. No. 5,574,355, issued Nov. 12, 1996, entitled METHOD AND APPARATUS FOR DETECTION AND CONTROL OF THERMAL RUNAWAY IN A BATTERY UNDER CHARGE; U.S. Pat. No. 5,585,416, issued Dec. 10, 1996, entitled APPARATUS AND METHOD FOR STEP-CHARGING BATTERIES TO OPTIMIZE CHARGE ACCEPTANCE; U.S. Pat. No. 5,585,728, issued Dec. 17, 1996, entitled ELECTRONIC BATTERY TESTER WITH AUTOMATIC COMPENSATION FOR LOW STATE-OF-CHARGE; U.S. Pat. No. 5,589,757, issued Dec. 31, 1996, entitled APPARATUS AND METHOD FOR STEP-CHARGING BATTERIES TO OPTIMIZE CHARGE ACCEPTANCE; U.S. Pat. No. 5,592,093, issued Jan. 7, 1997, entitled ELECTRONIC BATTERY TESTING DEVICE LOOSE TERMINAL CONNECTION DETECTION VIA A COMPARISON CIRCUIT; U.S. Pat. No. 5,598,098, issued Jan. 28, 1997, entitled ELECTRONIC BATTERY TESTER WITH VERY HIGH NOISE IMMUNITY; U.S. Pat. No. 5,656,920, issued Aug. 12, 1997, entitled METHOD FOR OPTIMIZING THE CHARGING LEAD-ACID BATTERIES AND AN INTERACTIVE CHARGER; U.S. Pat. No. 5,757,192, issued May 26, 1998, entitled METHOD AND APPARATUS FOR DETECTING A BAD CELL IN A STORAGE BATTERY; U.S. Pat. No. 5,821,756, issued Oct. 13, 1998, entitled ELECTRONIC BATTERY TESTER WITH TAILORED COMPENSATION FOR LOW STATE-OF CHARGE; U.S. Pat. No. 5,831,435, issued Nov. 3, 1998, entitled BATTERY TESTER FOR JIS STANDARD; U.S. Pat. No. 5,871,858, issued Feb. 16, 1999, entitled ANTI-THEFT BATTERY; U.S. Pat. No. 5,914,605, issued Jun. 22, 1999, entitled ELECTRONIC BATTERY TESTER; U.S. Pat. No. 5,945,829, issued Aug. 31, 1999, entitled MIDPOINT BATTERY MONITORING; U.S. Pat. No. 6,002,238, issued Dec. 14, 1999, entitled METHOD AND APPARATUS FOR MEASURING COMPLEX IMPEDANCE OF CELLS AND BATTERIES; U.S. Pat. No. 6,037,751, issued Mar. 14, 2000, entitled APPARATUS FOR CHARGING BATTERIES; U.S. Pat. No. 6,037,777, issued Mar. 14, 2000, entitled METHOD AND APPARATUS FOR DETERMINING BATTERY PROPERTIES FROM COMPLEX IMPEDANCE/ADMITTANCE; U.S. Pat. No. 6,051,976, issued Apr. 18, 2000, entitled METHOD AND APPARATUS FOR AUDITING A BATTERY TEST; U.S. Pat. No. 6,081,098, issued Jun. 27, 2000, entitled METHOD AND APPARATUS FOR CHARGING A BATTERY; U.S. Pat. No. 6,091,245, issued Jul. 18, 2000, entitled METHOD AND APPARATUS FOR AUDITING A BATTERY TEST; U.S. Pat. No. 6,104,167, issued Aug. 15, 2000, entitled METHOD AND APPARATUS FOR CHARGING A BATTERY; U.S. Pat. No. 6,137,269, issued Oct. 24, 2000, entitled METHOD AND APPARATUS FOR ELECTRONICALLY EVALUATING THE INTERNAL TEMPERATURE OF AN ELECTROCHEMICAL CELL OR BATTERY; U.S. Pat. No. 6,163,156, issued Dec. 19, 2000, entitled ELECTRICAL CONNECTION FOR ELECTRONIC BATTERY TESTER; U.S. Pat. No. 6,172,483, issued Jan. 9, 2001, entitled METHOD AND APPARATUS FOR MEASURING COMPLEX IMPEDANCE OF CELLS AND BATTERIES; U.S. Pat. No. 6,172,505, issued Jan. 9, 2001, entitled ELECTRONIC BATTERY TESTER; U.S. Pat. No. 6,222,369, issued Apr. 24, 2001, entitled METHOD AND APPARATUS FOR DETERMINING BATTERY PROPERTIES FROM COMPLEX IMPEDANCE/ADMITTANCE; U.S. Pat. No. 6,225,808, issued May 1, 2001, entitled TEST COUNTER FOR ELECTRONIC BATTERY TESTER; U.S. Pat. No. 6,249,124, issued Jun. 19, 2001, entitled ELECTRONIC BATTERY TESTER WITH INTERNAL BATTERY; U.S. Pat. No. 6,259,254, issued Jul. 10, 2001, entitled APPARATUS AND METHOD FOR CARRYING OUT DIAGNOSTIC TESTS ON BATTERIES AND FOR RAPIDLY CHARGING BATTERIES; U.S. Pat. No. 6,262,563, issued Jul. 17, 2001, entitled METHOD AND APPARATUS FOR MEASURING COMPLEX ADMITTANCE OF CELLS AND BATTERIES; U.S. Pat. No. 6,294,896, issued Sep. 25, 2001; entitled METHOD AND APPARATUS FOR MEASURING COMPLEX SELF-IMMITANCE OF A GENERAL ELECTRICAL ELEMENT; U.S. Pat. No. 6,294,897, issued Sep. 25, 2001, entitled METHOD AND APPARATUS FOR ELECTRONICALLY EVALUATING THE INTERNAL TEMPERATURE OF AN ELECTROCHEMICAL CELL OR BATTERY; U.S. Pat. No. 6,304,087, issued Oct. 16, 2001, entitled APPARATUS FOR CALIBRATING ELECTRONIC BATTERY TESTER; U.S. Pat. No. 6,310,481, issued Oct. 30, 2001, entitled ELECTRONIC BATTERY TESTER; U.S. Pat. No. 6,313,607, issued Nov. 6, 2001, entitled METHOD AND APPARATUS FOR EVALUATING STORED CHARGE IN AN ELECTROCHEMICAL CELL OR BATTERY; U.S. Pat. No. 6,313,608, issued Nov. 6, 2001, entitled METHOD AND APPARATUS FOR CHARGING A BATTERY; U.S. Pat. No. 6,316,914, issued Nov. 13, 2001, entitled TESTING PARALLEL STRINGS OF STORAGE BATTERIES; U.S. Pat. No. 6,323,650, issued Nov. 27, 2001, entitled ELECTRONIC BATTERY TESTER; U.S. Pat. No. 6,329,793, issued Dec. 11, 2001, entitled METHOD AND APPARATUS FOR CHARGING A BATTERY; U.S. Pat. No. 6,331,762, issued Dec. 18, 2001, entitled ENERGY MANAGEMENT SYSTEM FOR AUTOMOTIVE VEHICLE; U.S. Pat. No. 6,332,113, issued Dec. 18, 2001, entitled ELECTRONIC BATTERY TESTER; U.S. Pat. No. 6,351,102, issued Feb. 26, 2002, entitled AUTOMOTIVE BATTERY CHARGING SYSTEM TESTER; U.S. Pat. No. 6,359,441, issued Mar. 19, 2002, entitled ELECTRONIC BATTERY TESTER; U.S. Pat. No. 6,363,303, issued Mar. 26, 2002, entitled ALTERNATOR DIAGNOSTIC SYSTEM; U.S. Pat. No. 6,377,031, issued Apr. 23, 2002, entitled INTELLIGENT SWITCH FOR POWER MANAGEMENT; U.S. Pat. No. 6,392,414, issued May 21, 2002, entitled ELECTRONIC BATTERY TESTER; U.S. Pat. No. 6,417,669, issued Jul. 9, 2002, entitled SUPPRESSING INTERFERENCE IN AC MEASUREMENTS OF CELLS, BATTERIES AND OTHER ELECTRICAL ELEMENTS; U.S. Pat. No. 6,424,158, issued Jul. 23, 2002, entitled APPARATUS AND METHOD FOR CARRYING OUT DIAGNOSTIC TESTS ON BATTERIES AND FOR RAPIDLY CHARGING BATTERIES; U.S. Pat. No. 6,441,585, issued Aug. 17, 2002, entitled APPARATUS AND METHOD FOR TESTING RECHARGEABLE ENERGY STORAGE BATTERIES; U.S. Pat. No. 6,437,957, issued Aug. 20, 2002, entitled SYSTEM AND METHOD FOR PROVIDING SURGE, SHORT, AND REVERSE POLARITY CONNECTION PROTECTION; U.S. Pat. No. 6,445,158, issued Sep. 3, 2002, entitled VEHICLE ELECTRICAL SYSTEM TESTER WITH ENCODED OUTPUT; U.S. Pat. No. 6,456,045, issued Sep. 24, 2002, entitled INTEGRATED CONDUCTANCE AND LOAD TEST BASED ELECTRONIC BATTERY TESTER; U.S. Pat. No. 6,466,025, issued Oct. 15, 2002, entitled ALTERNATOR TESTER; U.S. Pat. No. 6,465,908, issued Oct. 15, 2002, entitled INTELLIGENT POWER MANAGEMENT SYSTEM; U.S. Pat. No. 6,466,026, issued Oct. 15, 2002, entitled PROGRAMMABLE CURRENT EXCITER FOR MEASURING AC IMMITTANCE OF CELLS AND BATTERIES; U.S. Pat. No. 6,469,511, issued Nov. 22, 2002, entitled BATTERY CLAMP WITH EMBEDDED ENVIRONMENT SENSOR; U.S. Pat. No. 6,495,990, issued Dec. 17, 2002, entitled METHOD AND APPARATUS FOR EVALUATING STORED CHARGE IN AN ELECTROCHEMICAL CELL OR BATTERY; U.S. Pat. No. 6,497,209, issued Dec. 24, 2002, entitled SYSTEM AND METHOD FOR PROTECTING A CRANKING SUBSYSTEM; U.S. Pat. No. 6,507,196, issued Jan. 14, 2003; entitled BATTERY HAVING DISCHARGE STATE INDICATION; U.S. Pat. No. 6,534,993, issued Mar. 18, 2003, entitled ELECTRONIC BATTERY TESTER; U.S. Pat. No. 6,544,078, issued Apr. 8, 2003, entitled BATTERY CLAMP WITH INTEGRATED CURRENT SENSOR; U.S. Pat. No. 6,556,019, issued Apr. 29, 2003, entitled ELECTRONIC BATTERY TESTER; U.S. Pat. No. 6,566,883, issued May 20, 2003, entitled ELECTRONIC BATTERY TESTER; U.S. Pat. No. 6,586,941, issued Jul. 1, 2003, entitled BATTERY TESTER WITH DATABUS; U.S. Pat. No. 6,597,150, issued Jul. 22, 2003, entitled METHOD OF DISTRIBUTING JUMP-START BOOSTER PACKS; U.S. Pat. No. 6,621,272, issued Sep. 16, 2003, entitled PROGRAMMABLE CURRENT EXCITER FOR MEASURING AC IMMITTANCE OF CELLS AND BATTERIES; U.S. Pat. No. 6,623,314, issued Sep. 23, 2003, entitled KELVIN CLAMP FOR ELECTRICALLY COUPLING TO A BATTERY CONTACT; U.S. Pat. No. 6,633,165, issued Oct. 14, 2003, entitled IN-VEHICLE BATTERY MONITOR; U.S. Pat. No. 6,635,974, issued Oct. 21, 2003, entitled SELF-LEARNING POWER MANAGEMENT SYSTEM AND METHOD; U.S. Pat. No. 6,707,303, issued Mar. 16, 2004, entitled ELECTRONIC BATTERY TESTER; U.S. Pat. No. 6,737,831, issued May 18, 2004, entitled METHOD AND APPARATUS USING A CIRCUIT MODEL TO EVALUATE CELL/BATTERY PARAMETERS; U.S. Pat. No. 6,744,149, issued Jun. 1, 2004, entitled SYSTEM AND METHOD FOR PROVIDING STEP-DOWN POWER CONVERSION USING AN INTELLIGENT SWITCH; U.S. Pat. No. 6,759,849, issued Jul. 6, 2004, entitled BATTERY TESTER CONFIGURED TO RECEIVE A REMOVABLE DIGITAL MODULE; U.S. Ser. No. 09/780,146, filed Feb. 9, 2001, entitled STORAGE BATTERY WITH INTEGRAL BATTERY TESTER; U.S. Ser. No. 09/756,638, filed Jan. 8, 2001, entitled METHOD AND APPARATUS FOR DETERMINING BATTERY PROPERTIES FROM COMPLEX IMPEDANCE/ADMITTANCE; U.S. Ser. No. 09/862,783, filed May 21, 2001, entitled METHOD AND APPARATUS FOR TESTING CELLS AND BATTERIES EMBEDDED IN SERIES/PARALLEL SYSTEMS; U.S. Ser. No. 09/880,473, filed Jun. 13, 2001; entitled BATTERY TEST MODULE; U.S. Ser. No. 60/348,479, filed Oct. 29, 2001, entitled CONCEPT FOR TESTING HIGH POWER VRLA BATTERIES; U.S. Ser. No. 10/046,659, filed Oct. 29, 2001, entitled ENERGY MANAGEMENT SYSTEM FOR AUTOMOTIVE VEHICLE; U.S. Ser. No. 09/993,468, filed Nov. 14, 2001, entitled KELVIN CONNECTOR FOR A BATTERY POST; U.S. Ser. No. 10/042,451, filed Jan. 8, 2002, entitled BATTERY CHARGE CONTROL DEVICE; U.S. Ser. No. 10/093,853, filed Mar. 7, 2002, entitled ELECTRONIC BATTERY TESTER WITH NETWORK COMMUNICATION; U.S. Ser. No. 10/098,741, filed Mar. 14, 2002, entitled METHOD AND APPARATUS FOR AUDITING A BATTERY TEST; U.S. Ser. No. 10/112,114, filed Mar. 28, 2002, entitled BOOSTER PACK WITH STORAGE CAPACITOR; U.S. Ser. No. 10/109,734, filed Mar. 28, 2002, entitled APPARATUS AND METHOD FOR COUNTERACTING SELF DISCHARGE IN A STORAGE BATTERY; U.S. Ser. No. 10/112,105, filed Mar. 28, 2002, entitled CHARGE CONTROL SYSTEM FOR A VEHICLE BATTERY; U.S. Ser. No. 10/112,998, filed Mar. 29, 2002, entitled BATTERY TESTER WITH BATTERY REPLACEMENT OUTPUT; U.S. Ser. No. 10/119,297, filed Apr. 9, 2002, entitled METHOD AND APPARATUS FOR TESTING CELLS AND BATTERIES EMBEDDED IN SERIES/PARALLEL SYSTEMS; U.S. Ser. No. 60/387,046, filed Jun. 7, 2002, entitled METHOD AND APPARATUS FOR INCREASING THE LIFE OF A STORAGE BATTERY; U.S. Ser. No. 10/177,635, filed Jun. 21, 2002, entitled BATTERY CHARGER WITH BOOSTER PACK; U.S. Ser. No. 10/200,041, filed Jul. 19, 2002, entitled AUTOMOTIVE VEHICLE ELECTRICAL SYSTEM DIAGNOSTIC DEVICE; U.S. Ser. No. 10/217,913, filed Aug. 13, 2002, entitled, BATTERY TEST MODULE; U.S. Ser. No. 10/246,439, filed Sep. 18, 2002, entitled BATTERY TESTER UPGRADE USING SOFTWARE KEY; U.S. Ser. No. 10/263,473, filed Oct. 2, 2002, entitled ELECTRONIC BATTERY TESTER WITH RELATIVE TEST OUTPUT; U.S. Ser. No. 10/271,342, filed Oct. 15, 2002, entitled IN-VEHICLE BATTERY MONITOR; U.S. Ser. No. 10/310,515, filed Dec. 5, 2002, entitled BATTERY TEST MODULE; U.S. Ser. No. 10/310,490, filed Dec. 5, 2002, entitled ELECTRONIC BATTERY TESTER; U.S. Ser. No. 10/310,385, filed Dec. 5, 2002, entitled BATTERY TEST MODULE; U.S. Ser. No. 60/437,224, filed Dec. 31, 2002, entitled DISCHARGE VOLTAGE PREDICTIONS; U.S. Ser. No. 10/349,053, filed Jan. 22, 2003, entitled APPARATUS AND METHOD FOR PROTECTING A BATTERY FROM OVERDISCHARGE; U.S. Ser. No. 10/388,855, filed Mar. 14, 2003, entitled ELECTRONIC BATTERY TESTER WITH BATTERY FAILURE TEMPERATURE DETERMINATION; U.S. Ser. No. 10/396,550, filed Mar. 25, 2003, entitled ELECTRONIC BATTERY TESTER; U.S. Ser. No. 60/467,872, filed May 5, 2003, entitled METHOD FOR DETERMINING BATTERY STATE OF CHARGE; U.S. Ser. No. 60/477,082, filed Jun. 9, 2003, entitled ALTERNATOR TESTER; U.S. Ser. No. 10/460,749, filed Jun. 12, 2003, entitled MODULAR BATTERY TESTER FOR SCAN TOOL; U.S. Ser. No. 10/462,323, filed Jun. 16, 2003, entitled ELECTRONIC BATTERY TESTER HAVING A USER INTERFACE TO CONFIGURE A PRINTER; U.S. Ser. No. 10/601,608, filed Jun. 23, 2003, entitled CABLE FOR ELECTRONIC BATTERY TESTER; U.S. Ser. No. 10/601,432, filed Jun. 23, 2003, entitled BATTERY TESTER CABLE WITH MEMORY; U.S. Ser. No. 60/490,153, filed Jul. 25, 2003, entitled SHUNT CONNECTION TO A PCB FOR AN ENERGY MANAGEMENT SYSTEM EMPLOYED IN AN AUTOMOTIVE VEHICLE; U.S. Ser. No. 10/653,342, filed Sep. 2, 2003, entitled ELECTRONIC BATTERY TESTER CONFIGURED TO PREDICT A LOAD TEST RESULT; U.S. Ser. No. 10/654,098, filed Sep. 3, 2003, entitled BATTERY TEST OUTPUTS ADJUSTED BASED UPON BATTERY TEMPERATURE AND THE STATE OF DISCHARGE OF THE BATTERY; U.S. Ser. No. 10/656,526, filed Sep. 5, 2003, entitled METHOD AND APPARATUS FOR MEASURING A PARAMETER OF A VEHICLE ELECTRICAL SYSTEM; U.S. Ser. No. 10/656,538, filed Sep. 5, 2003, entitled ALTERNATOR TESTER WITH ENCODED OUTPUT; U.S. Ser. No. 10/675,933, filed Sep. 30, 2003, entitled QUERY BASED ELECTRONIC BATTERY TESTER; U.S. Ser. No. 10/678,629, filed Oct. 3, 2003, entitled ELECTRONIC BATTERY TESTER/CHARGER WITH INTEGRATED BATTERY CELL TEMPERATURE MEASUREMENT DEVICE; U.S. Ser. No. 10/441,271, filed May 19, 2003, entitled ELECTRONIC BATTERY TESTER; U.S. Ser. No. 09/653,963, filed Sep. 1, 2000, entitled SYSTEM AND METHOD FOR CONTROLLING POWER GENERATION AND STORAGE; U.S. Ser. No. 10/174,110, filed Jun. 18, 2002, entitled DAYTIME RUNNING LIGHT CONTROL USING AN INTELLIGENT POWER MANAGEMENT SYSTEM; U.S. Ser. No. 60/488,775, filed Jul. 21, 2003, entitled ULTRASONICALLY ASSISTED CHARGING; U.S. Ser. No. 10/258,441, filed Apr. 9, 2003, entitled CURRENT MEASURING CIRCUIT SUITED FOR BATTERIES; U.S. Ser. No. 10/705,020, filed Nov. 11, 2003, entitled APPARATUS AND METHOD FOR SIMULATING A BATTERY TESTER WITH A FIXED RESISTANCE LOAD; U.S. Ser. No. 10/681,666, filed Oct. 8, 2003, entitled ELECTRONIC BATTERY TESTER WITH PROBE LIGHT; U.S. Ser. No. 10/748,792, filed Dec. 30, 2003, entitled APPARATUS AND METHOD FOR PREDICTING THE REMAINING DISCHARGE TIME OF A BATTERY; U.S. Ser. No. 10/767,945, filed Jan. 29, 2004, entitled ELECTRONIC BATTERY TESTER; U.S. Ser. No. 10/783,682, filed Feb. 20, 2004, entitled REPLACEABLE CLAMP FOR ELECTRONIC BATTERY TESTER; U.S. Ser. No. 60/548,513, filed Feb. 27, 2004, entitled WIRELESS BATTERY MONITOR; U.S. Ser. No. 10/791,141, filed Mar. 2, 2004, entitled METHOD AND APPARATUS FOR AUDITING A BATTERY TEST; U.S. Ser. No. 60/557,366, filed Mar. 29, 2004, entitled BATTERY MONITORING SYSTEM WITHOUT CURRENT MEASUREMENT; U.S. Ser. No. 10/823,140, filed Apr. 13, 2004, entitled THEFT PREVENTION DEVICE FOR AUTOMOTIVE VEHICLE SERVICE CENTERS; U.S. Ser. No. 60/575,945, filed Jun. 1, 2004, entitled BATTERY TESTER CAPABLE OF IDENTIFYING FAULTY BATTERY POST ADAPTERS; U.S. Ser. No. 60/577,345, filed Jun. 4, 2004, entitled NEW METHOD FOR AUTOMATICALLY TESTING A BATTERY AND TRANSMITTING DATA TO ANOTHER MODULE IN A VEHICLE; U.S. Ser. No. 10/864,904, filed Jun. 9, 2004, entitled ALTERNATOR TESTER; U.S. Ser. No. 10/867,385, filed Jun. 14, 2004, entitled ENERGY MANAGEMENT SYSTEM FOR AUTOMOTIVE VEHICLE; U.S. Ser. No. 10/870,680, filed Jun. 17, 2004, entitled ELECTRONIC BATTERY TESTER WITH RELATIVE TEST OUTPUT; U.S. Ser. No. 60/582,925, filed Jun. 25, 2004, entitled BATTERY TESTER WITH BATTERY POTENTIAL FOR RECOVERY OUTPUT; U.S. Ser. No. 10/883,019, filed Jul. 1, 2004, entitled MODULAR ELECTRONIC BATTERY TESTER; U.S. Ser. No. 60/585,700, filed Jul. 6, 2004, entitled TEST STATION; U.S. Ser. No. 60/587,232, filed Jul. 12, 2004, entitled WIRELESS BATTERY TESTER; which are incorporated herein in their entirety.

In general, battery testing techniques have used a single, integrated stand-alone unit.

SUMMARY OF THE INVENTION

A cable for connecting to an electronic battery tester is configured to couple to a databus of a vehicle to the electronic battery tester. Electrical connection extending between ends of the cables configured to couple the electronic battery tester to the databus of the vehicle.

DETAILED DESCRIPTION OF THE PREFERRED EMBODIMENTS

Figure 1:
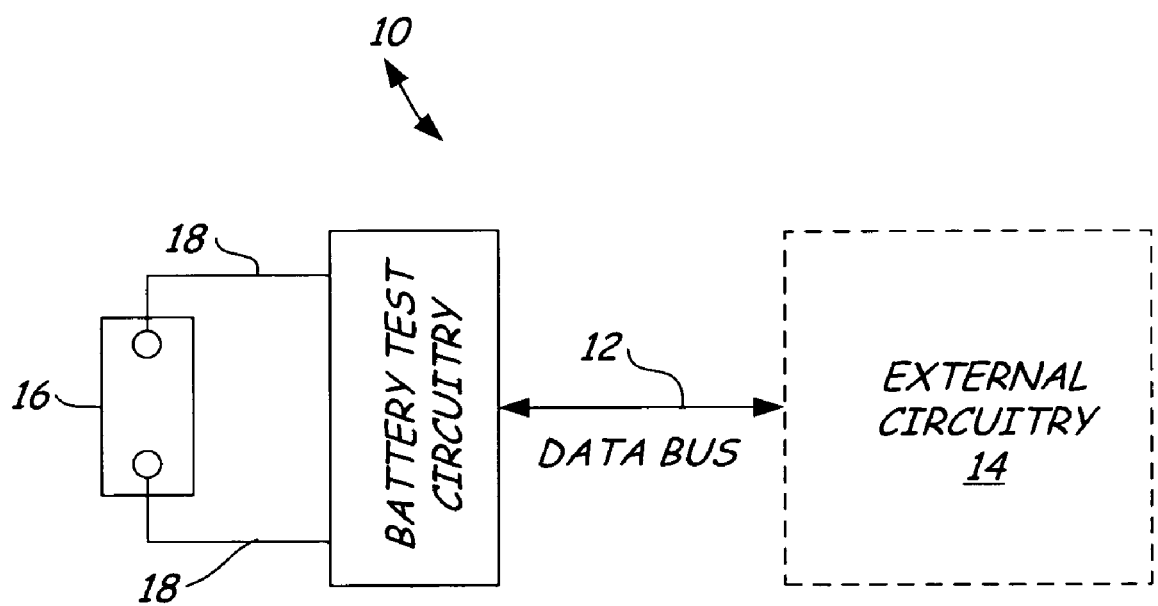
FIG. 1 is a simplified block diagram showing battery test circuitry coupled to external circuitry through a databus.

Typically, battery testers have been stand-alone units. The present invention provides a battery tester 10 such as that illustrated in FIG. 1 which includes a databus 12 for coupling to external circuitry 14. Battery tester 10 is configured to couple to storage battery 16 through electrical connectors 18 to perform a battery test on battery 16. Connectors 18 can be, for example, Kelvin type connectors. Typically, test circuitry 10 will obtain a dynamic parameter of the battery using an AC forcing function. Examples include dynamic conductance, resistance, admittance, impedance, their combinations, or others. However, any type of battery test can be performed including battery testing which involves application of large loads, or application of large currents or voltages such as through a charger, simple voltage measurements, etc. In one embodiment, the battery tester 10 is permanently mounted in a automotive vehicle such as the type of vehicle that uses a internal combustion engine or an electric engine.

Databus 12 is used to exchange information with external circuitry 14. Such information includes, for example, raw data measurements and conclusions of battery tester 10, and inputs, such as user inputs and other sensor inputs into battery tester 10. Further, external circuitry 14 can control battery tester 10 through databus 12 and provide information such as a battery rating to battery tester 10 for use in performing a battery test. Databus 12 can be a proprietary databus or can be in accordance with known standards such as RS232, CAN, ISA, PCI, PCMCIA, etc. Battery tester 10 can be configured to communicate with portable devices such as portable notebook computers, PDAs (Personal Data Assistants) such as a Palm Pilot™, etc. The databus 12 can also be configured to interface with other types of equipment which are used in the automotive industry such as "scan" tools which are used to interface with the on-board computer in a vehicle. Such scan tools are known in the art and are used to perform diagnostics and retrieve information from the on-board computer. In such an embodiment, databus 12 can be in accordance with the databus used in OBD (on-board diagnostic) systems.

Figure 2:
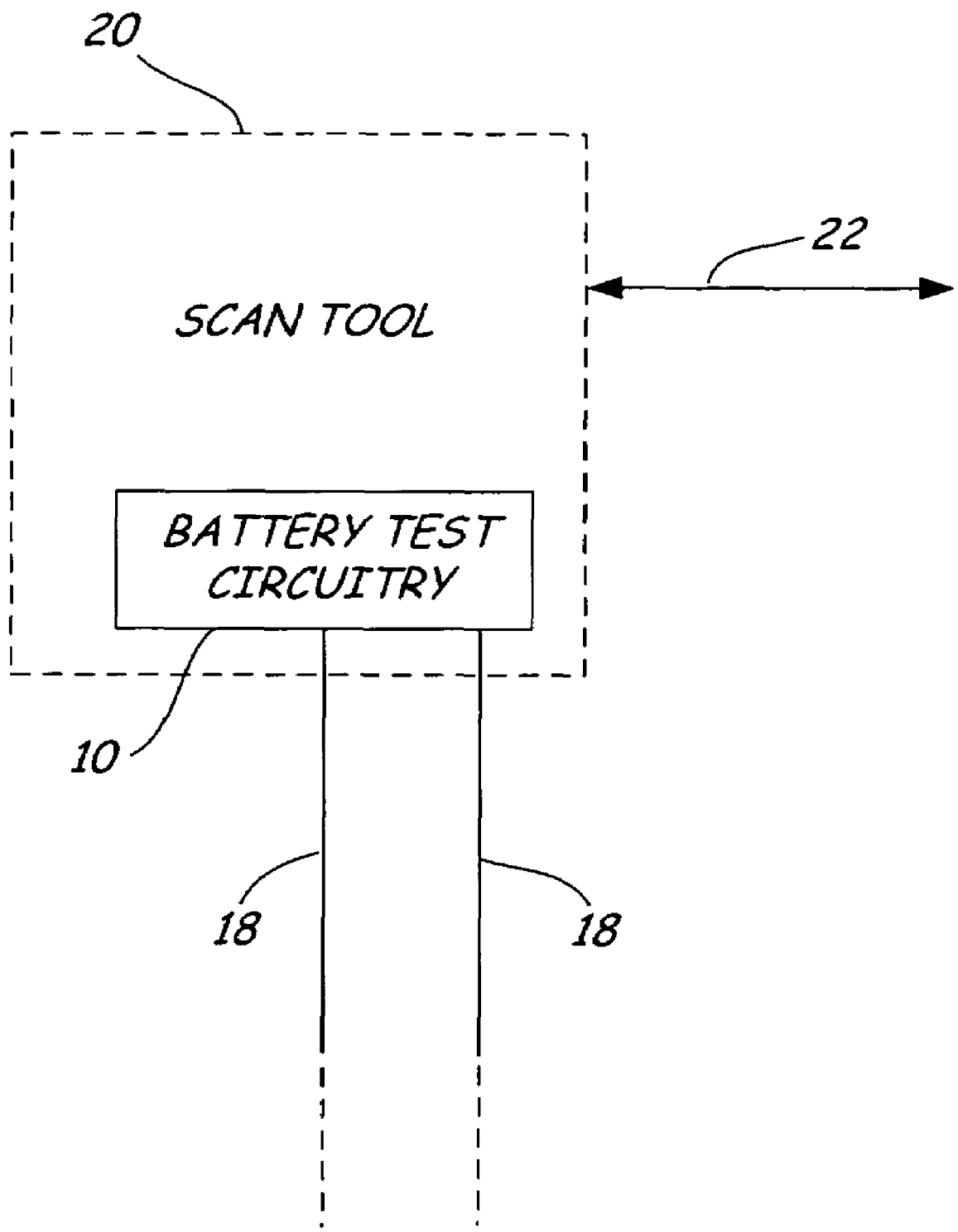
FIG. 2 is a simplified block diagram showing a scan tool which is one type of external circuitry shown in FIG. 1.

The battery tester 10 of FIG. 1 can be a modular component of a scan tool formed by external circuitry 14. In another aspect of the invention as illustrated in FIG. 2, the battery tester 10 is an integral component of a scan tool 20. FIG. 2 also illustrates a second databus 22 which is used to couple to an on-board computer of a vehicle.

In embodiments which utilize a scan tool, an operator is able to perform a battery test using the same scan tool used for diagnosing other conditions of the vehicle. Further, the scan tool can selectively instruct an operator to perform a battery test or control operation of the battery test based upon data retrieved from the on-board vehicle computer system through bus 22. This can be part of an overall diagnostic system used to provide more accurate diagnostics of the vehicle. In one embodiment, the battery test circuitry requires information through bus 22 or monitors the flow of information on a databus of the vehicle. The test circuit can obtain information about battery type, battery rating, and charge history. Additionally, if the vehicle contains an internal battery tester, information regarding battery tests or battery measurements can be obtained or monitored through bus 22. In such an embodiment, test circuit 10 does not need to perform a battery test itself, or couple to the battery.

Figure 3:
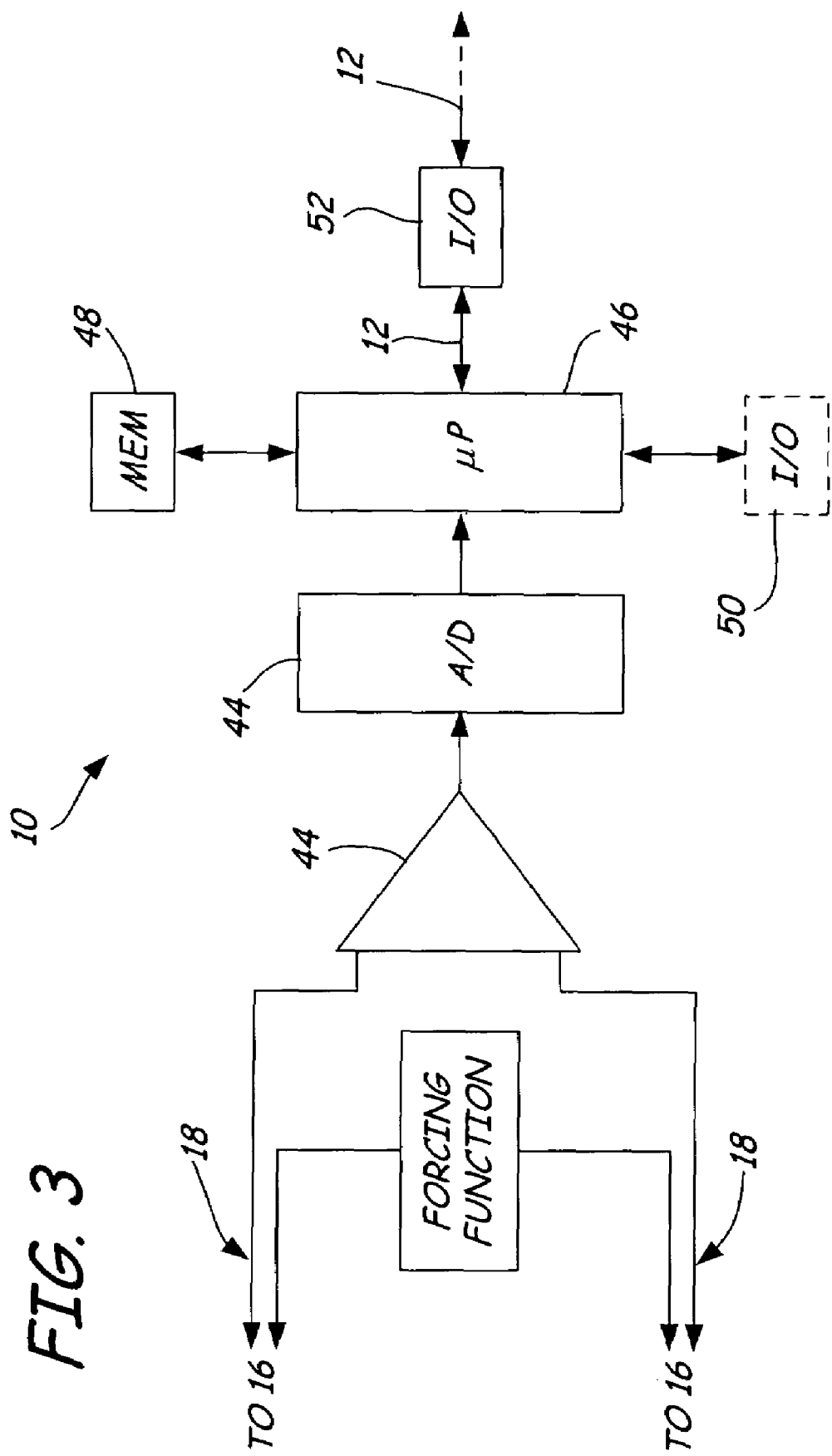
FIG. 3 is a simplified block diagram showing battery test circuitry.

FIG. 3 is a more detailed block diagram of battery test circuitry 10 which includes a forcing function 40 and an amplifier 42 coupled to connectors 18. In the illustration of FIG. 3, connectors 18 are shown as Kelvin connections. The forcing function 40 can be any type of signal which has a time varying component including a transient signal. The forcing function can be through application of a load or by applying an active signal to battery 16. A response signal is sensed by amplifier 42 and provided to analog to digital converter 44 which couples to microprocessor 46. Microprocessor 46 operates in accordance with instructions stored in memory 48. In accordance with the invention, microprocessor 46 can store data into memory 48.

Input/output (I/O) is provided for coupling to the databus 12. I/O 102 can be in accordance with the desired standard or protocol as described above. Data collected by battery test circuitry 10 can be stored in memory 48 and transmitted over bus 12 when pulled by external circuitry 14. In one embodiment, input/output 52 comprises an RF (Radio Frequency) or IR (Infrared) input/output circuit and bus 12 comprises electromagnetic radiation. The logged data can comprise individual measurement points such as voltage and/or current measurements, either static or dynamic. Additionally, the logged data can comprise time and data information, operating conditions such as temperature, charge, etc. In addition to logging raw data, calculated data such as calculated conductance or battery condition, battery state of health, battery state of charge, etc. can be logged.

Of course, the illustration of FIG. 3 is simply one simplified embodiment and other embodiments are in accordance with the invention. Databus 12 may be capable of coupling directly to memory 48 for retrieval of stored data. Additionally, in the illustrated embodiment microprocessor 46 is configured to measure a dynamic parameter based upon the forcing function 40. This dynamic parameter can be correlated with battery condition as set forth in the above-mentioned Champlin and Midtronics, Inc. patents. However, other types of battery tests circuitry can be used in the present invention and certain aspects of the invention should not be limited to the specific embodiment illustrated herein. FIG. 3 also illustrates an optional input/output block 50 which can be any other type of input and/or output coupled to microprocessor 46. For example, this can be used to couple to external devices or to facilitate user input and/or output. Databus 12 can also be used to provide data or instructions to microprocessor 46. This can instruct the microprocessor 46 to perform a certain test, transmit specified data, update programming instructions, constant test parameters, etc. stored in memory 48. Although a microprocessor 46 is shown, other types of computational or other circuitry can be used to collect and place data into memory 48.

In one embodiment, I/O 50 comprises an interface to a removable digital storage medium, for example a Secure Digital (SD) card. Similarly, the I/O 50 can be configured to provide a multimedia interface to an MMC card. The databus 12 can be in accordance with any particular standard or otherwise for use in communicating with a scan tool. Additional examples includes RS-485, current loops, J1939, J1850 or a CAN bus.

Figure 4:
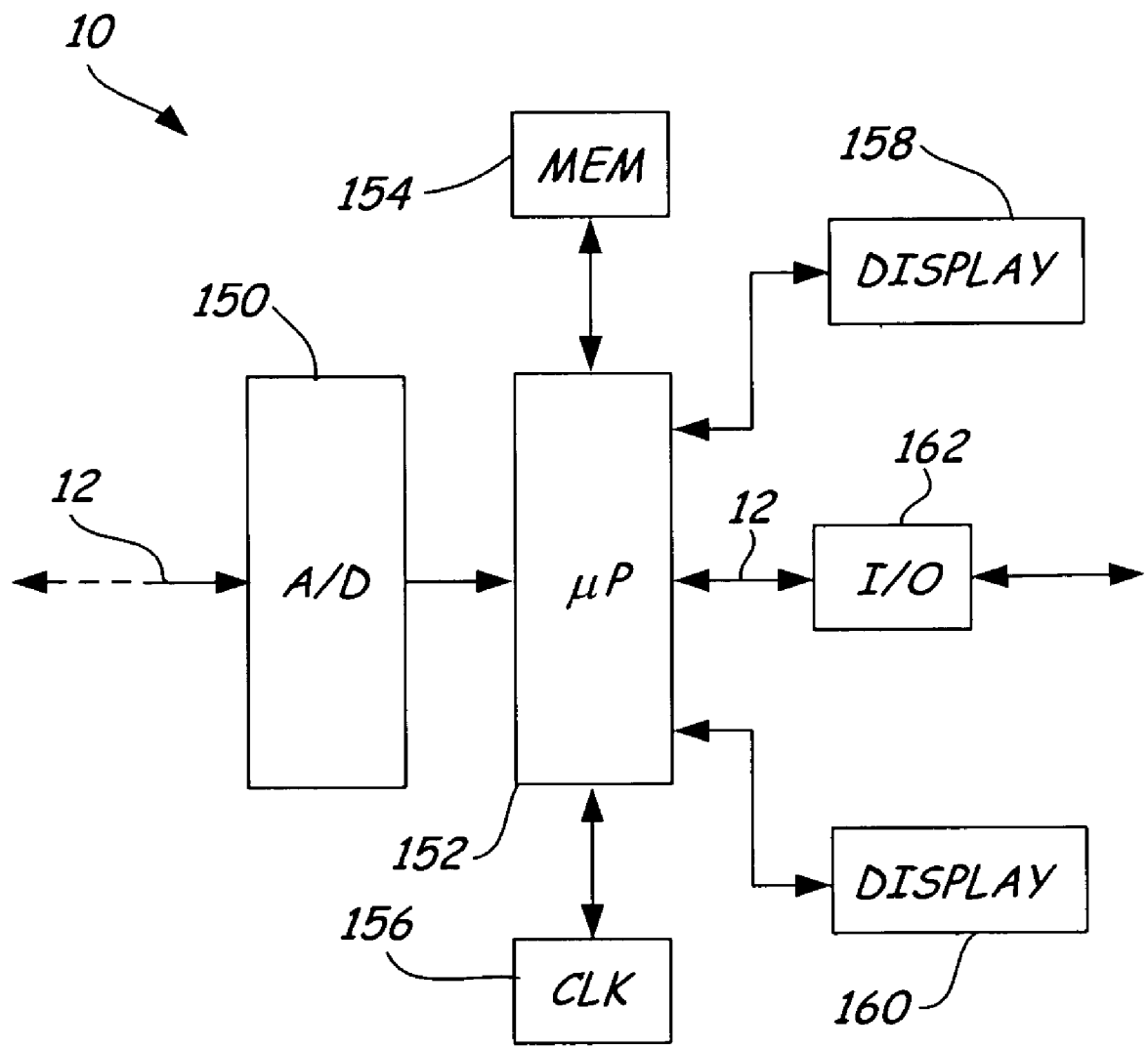
FIG. 4 is a simplified block diagram of external circuitry configured to couple to the battery test circuitry of FIG. 3.

FIG. 4 is a more detailed block diagram of external circuitry 14. External circuitry 14 includes input/output (I/O) circuitry 150 for coupling to databus 12. Again, if databus 12 is through a non-physical connections such as infrared or radio frequency, I/O circuitry 150 should operate accordingly. A microprocessor 152 couples to memory 154 and operates at a rate determined by a system clock 156. Microprocessor 152 can provide an output through display 158 and receive input from an operator through input 160. In operation, circuitry 14 is operably coupled to battery test circuitry through databus 12 and is configured to send and receive information through databus 12. An operator can instruct microprocessor 152 or microprocessor 152 can operate automatically, to retrieve data from memory 48 in battery test circuitry 10. The microprocessor 152 can process the data to calculate battery condition and follow trends in the measured values retrieved from memory 48. This information can be used to diagnose the condition of the battery 16 as well as use a charge and discharge history experienced by battery 16. Further, the information can be used to validate warranty claims in which a battery is returned to a manufacturer under a claim that it is defective.

External circuitry 14 can include additional input, output or input/output circuits 162 for communication using other techniques. For example, data can be sent to a printer or other computer system. Any type of data link can be used including modems, Ethernet or networking connections, etc.

In one embodiment, the external circuitry 14 comprises a personal data assistant (PDA) such as a Palm Pilot™. In such an embodiment, I/O 100 in battery test circuitry 10 can comprise a cradle which is adapted to receive the PDA. In such an embodiment, the PDA can simply be "dropped" into the cradle in order to exchange data with test circuitry 10. Similarly, many PDAs include an infrared or RF link which can be used to exchange data with battery test circuitry 10.

As discussed above, the battery tester circuitry 10 can be a modular component of a scan tool. For example, that scan tool can comprise external circuitry 14 shown in FIG. 1 and the databus 12 can be part of a cabling connection between the battery test circuitry 10 and the scan tool 14. In such an embodiment, there are a number of implementations of the present invention. In one aspect, all of the test circuitry necessary for performing a battery test if contained in the battery test circuitry 10. The final result of the battery test is provided to the scan tool 14 over the databus. Further, operator instructions or display data can be provided to the scan tool 14 and the battery test circuitry 10 can utilize a display 158, I/O 162, input 160 or other circuitry available in the scan tool 14. In another example, the microprocessor 152 of the scan tool 14 performs any calculations used in a battery test, and the battery test circuitry 10 includes less complex components such as the analog components required for performing a battery test. For example, the test circuitry 10 can contain the forcing function 40 and sensor 42. Analog values can be provided to the scan tool 14 and then digitize the received analog values. In another example, the analog values are digitized within the battery test circuitry 10 and provides it in a digital format to the scan tool 14. In another example embodiment, microprocessor 46 of the battery test circuitry 10 and microprocessor 152 of scan tool 14 are both utilized in a battery test. For example, the microprocessor 152 of the scan tool 14 can compute conversions between various rating systems, particular test requirements for certain types of vehicles or batteries or other higher level functions. The microprocessor 46 of the battery test circuitry 10 determines the initial battery test results.

In other example embodiments, the battery test circuitry 10 continually broadcasts voltage and/or conductance, current and/or conductance measurements of the databus 12. The battery test circuitry 10 can have an internal power source, be powered from the battery under test 16, or receive power from the scan tool 14. The databus 12 can be used to carry text messages to scan tool 14 for display on display 158 or in another manner. In another example, the memory 154 of the scan tool 14 contains a set of messages. A token or other short hand representation of a text message is transmitted from the battery test circuitry to the scan tool 14 on databus 12. This causes the microprocessor 152 to retrieve a selected message from the memory 154 which can then be displayed on display 158 or otherwise provided as an output. In one embodiment, the battery test circuitry provides an indication of the relative condition of the battery, for example, "good", "good/recharge", "charge and retest", or "replace battery". Another example condition is "bad cell-replace". If text messages are contained in a memory of the battery tester 10, the text can be in an appropriate language for the consumer.

In various aspects, the battery test circuitry 10 does not use Kelvin connections. In another example embodiment, a small or large load is included in the battery test circuitry 10. The load is used to apply a load test to the battery. In such an embodiment, the battery test circuitry may operate exclusively based upon such a load test and does not include circuitry to measure a dynamic parameter of the battery 12. In another example, the battery test is based upon a load test as well as a dynamic parameter based test. In another example, the battery test circuitry 10 includes a display for locally displaying information. One type of display includes a simple optical output such as that provided by one or more LEDs. The color or number of LEDs can indicate the result of a battery test. In some embodiments information beyond a battery test can be displayed by the scan tool 14. For example, the scan tool can display voltage, conductance, battery condition, battery cold cranking amps (CCA), a minimum or a maximum sensed voltage, or other measurements. The battery test circuitry 10 can be integrated with a cable that plugs into the scan tool 14. For example, the battery test circuitry 10 can be included in a small housing having one cable for connection to the scan tool 14 and another cable or cables for connections to the battery 12.

In some embodiments, battery test circuitry 10 can include circuitry configured to charge battery 16. In such embodiments, memory 48 can be used to log information regarding any charge which is applied to battery 16.

Figure 5:
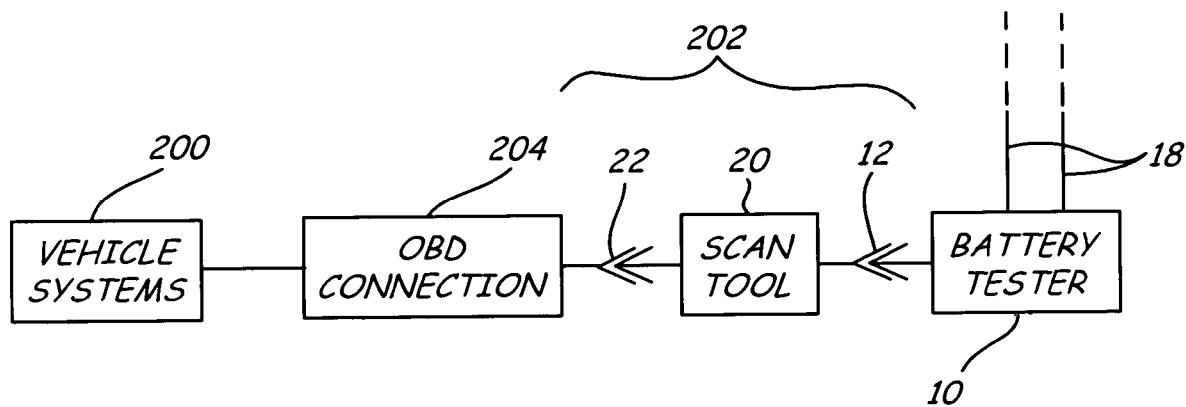
FIG. 5 is a simplified block diagram showing connection of a battery tester to an on board database of a vehicle via a scan tool.
Figure 6:
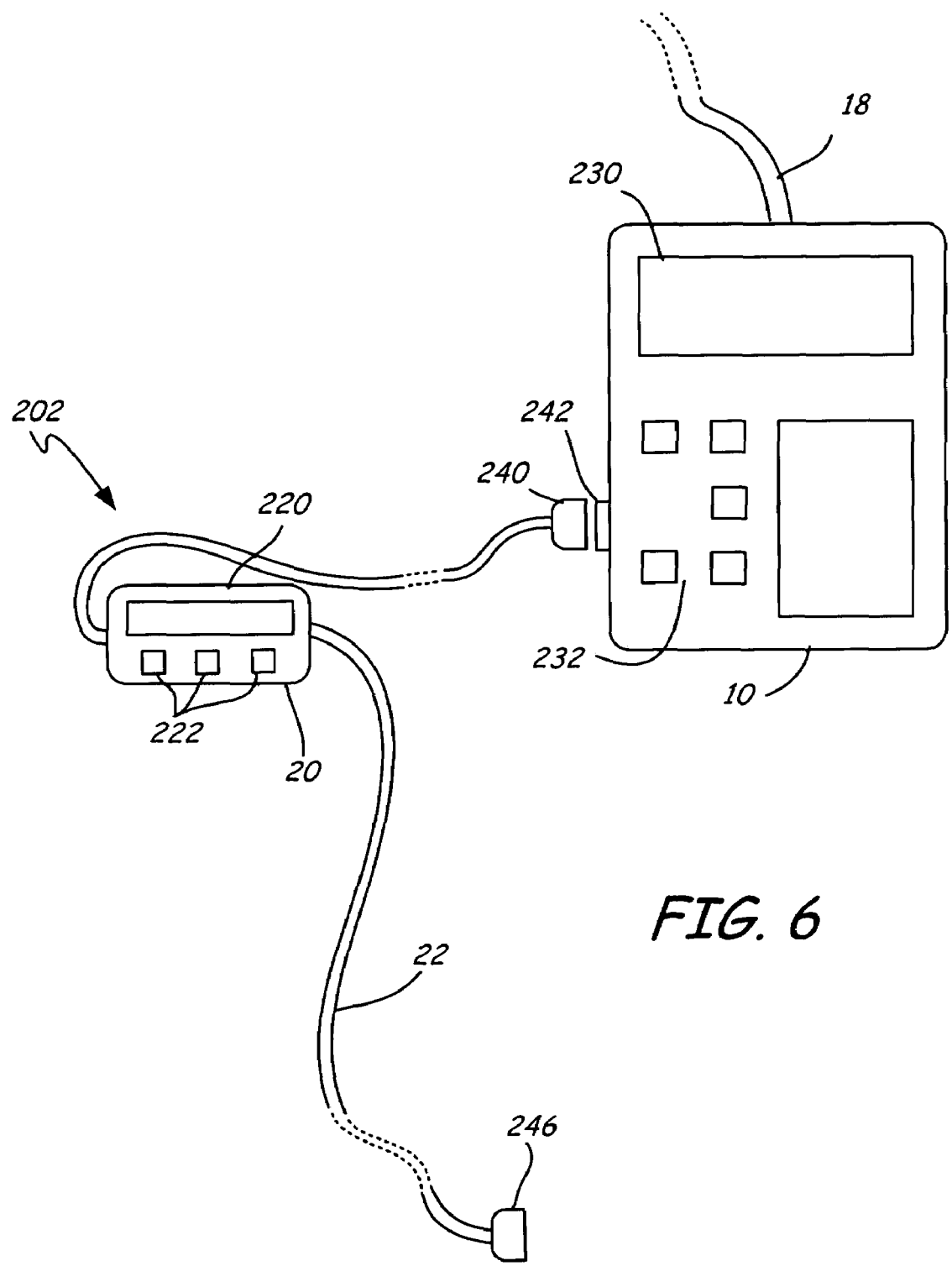
FIG. 6 is a perspective view of a cable including a scan tool used to couple a battery tester to a vehicle.

FIG. 5 is another example embodiment of the present invention in which a scan tool 20 is used to couple the battery test circuitry 10 to vehicle systems 200. The scan tool 20 can be embodied, for example, in a cable 202. The scan tool 20 couples to vehicle electrical systems 200 through, for example, the on board diagnostic connection 204 to the vehicle. Battery tester circuitry 10 couples to the scan tool 20 through a databus 12. It can be, for example, plugged in to the scan tool 20. Kelvin connections 18 are also provided for coupling to a battery in performing a battery test. FIG. 6 is a view of the battery tester circuitry 10 configured to couple to cable 202 which contains scan tool 20. Scan tool 20 is shown with an optional display 220 and user inputs 222 such as buttons. The battery tester 10 is illustrated as having a display 230 and user input buttons 232. Other types input output configurations can also be provided. Cable 202 includes a plug 240 configured to plug into plug 242 on battery tester 10. Further, cable 202 includes an OBD plug 246 configured to plug into an OBD connection on a vehicle. During operation, the scan tool 20 can be operated using the display 220 and the input buttons 222, if provided, or by circuitry within battery tester circuitry 10. In some embodiments, the cable 202 simply provides an interface between the tester 10 and the vehicle database and any scan tool functionality is performed within the battery tester circuitry 10. In another embodiment, active electronics are provided within the cable 202 to provide data conversion, scan tool functions and/or other functionality as desired.

Figure 7:
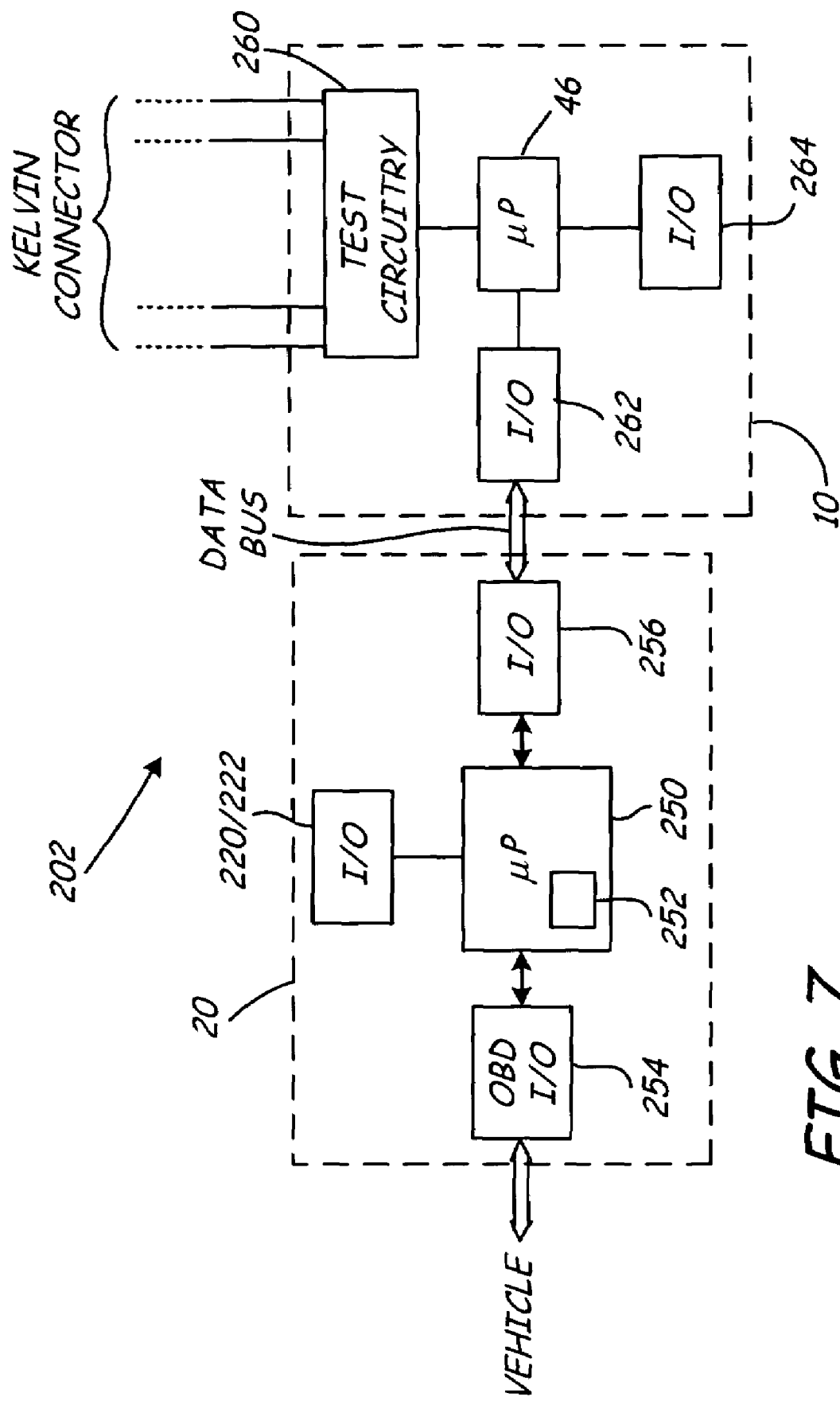
FIG. 7 is a simplified block diagram of the scan tool and battery tester shown in FIG. 6.

FIG. 7 is a blocked diagram showing various components illustrated in FIG. 6. In FIG. 7, the scan tool 20 includes a microprocessor 250 having a memory 252. OBD input/output circuitry 254 is provided for coupling to the on board database of the vehicle. IO circuitry 256 is used for communication with battery tester 10. Data in memory 252 can be updated by the battery tester, for example through the use of a smart card or other digital storage device. Battery tester 10 includes I/O circuitry 262 for coupling to the scan tool 20. The microprocessor 46 couples to test circuitry 260 and input/output circuitry 264. Test circuitry 260 is illustrated as a block diagram representation of the test circuitry used to perform a battery test through a Kelvin connection. The test circuitry can be analog and/or digital circuitry and may be, for example, partially implemented in microprocessor 46. The scan tool circuitry can receive power from an internal or external source including receiving power from the electronic battery tester.

Although the various connections between components shown here are illustrated as being wire connections, the invention is also applicable with wireless connections such as using rf, ir, inductive coupling or through other techniques. By providing the battery test circuitry with access to the on board database of the vehicle, additional information can be garnered regarding operation of the vehicle and, in some configurations, operation of the vehicle can be controlled or otherwise configured. In another example configuration, the IO circuitry to communicate with a smart card or other storage medium for use in updating software within the scan tool and/or battery tester.

Although the present invention has been described with reference to preferred embodiments, workers skilled in the art will recognize that changes may be made in form and detail without departing from the spirit and scope of the invention. For example, any type of battery test or battery test circuitry can be used by battery tester 10. Further, the databus 12 can be in accordance with any databus technique and should not be limited to the examples set forth herein. In various embodiments, battery tester 10 can be powered through power received through battery 16 or can be powered through power received through databus 12 or from a scan tool.

What is claimed is:

1. A scan tool for connecting to a databus of vehicle and to an electronic battery tester, comprising:
   a first connector configured to couple to the databus of a vehicle;
   a second connector configured to couple to the electronic battery tester, the electronic battery tester including a battery connector configured to couple to couple to a battery of the vehicle; and
   scan tool circuitry configured to couple the first connector to the second connector, the scan tool including a microprocessor configured to perform diagnostics on the vehicle through the first electrical connector to the vehicle, the scan tool circuitry further configured to communicate with the battery tester through the second connector.

2. The apparatus of claim 1 wherein the scan tool circuitry includes an On-board Diagnostic (OBD) interface.

3. The apparatus of claim 1 wherein the scan tool circuitry includes a battery tester I/O circuit.

4. The apparatus of claim 1 wherein the scan tool circuitry includes a memory.

5. The apparatus of claim 4 wherein the memory is configured to store information received from the battery tester.

6. The apparatus of claim 1 wherein the scan tool circuitry includes a user input.

7. The apparatus of claim 1 wherein the scan tool circuitry includes a display.

8. An electronic battery tester configured to couple to the second connector of the scan tool of claim 1.

9. The apparatus of claim 8 including a Kelvin connection configured to couple to the battery.

10. The apparatus of claim 8 wherein the battery tester is configured to measure a dynamic parameter of the battery as a function of an applied forcing function.

11. The apparatus of claim 8 wherein the battery tester is configured to transmit instructions to the scan tool.

12. A method for connecting an electronic battery tester to a data bus of a vehicle, comprising:
   coupling a first connector of a scan tool to the data bus of the vehicle, the scan tool including scan tool circuitry configured to perform diagnostics on the vehicle through the connection to the databus;
   coupling a second end of the cable to the electronic battery tester;
   coupling the battery tester to a battery of the vehicle using a battery connector of the battery tester;
   diagnosing operation of the vehicle using the scan tool circuitry;
   performing a battery test on the battery of the vehicle using the scan tool circuitry; and
   communicating between the scan tool and the electronic battery tester through the second end of the cable.

13. The method of claim 12 wherein the scan tool circuitry includes an On-board Diagnostic (OBD) interface.

14. The method of claim 12 wherein the scan tool circuitry includes a microprocessor.

15. The method of claim 12 wherein the scan tool circuitry includes a battery tester I/O circuit.

16. The method of claim 12 including storing information in a memory of the scan tool circuitry.

17. The method of claim 16 wherein the memory is configured to store information received from the battery tester.

18. The method of claim 14 including receiving a user input.

19. The method of claim 14 including displaying information on a display of the scan tool circuitry.

20. The method of claim 12 wherein performing the battery test includes measuring a parameter of the battery through Kelvin connections coupled to the battery.

21. The method of claim 20 including measuring a dynamic parameter of the battery as a function of an applied forcing function.

22. The method of claim 14 including transmitting instructions to the scan tool from the battery tester.

23. A scan tool for connecting an electronic battery tester to a data bus of a vehicle, comprising:
   means for electrically coupling to the databus of the vehicle;
   means for electrically coupling to the electronic battery tester; and
   scan tool circuitry means coupled between the means for electrically coupling to the data bus of the vehicle and the means for electrically coupling to the electronic battery tester for communication with the data bus of the vehicle, for interfacing with electronic circuitry in the electronic battery tester and performing a battery test on a battery of the vehicle using the means for electrically coupling to the electronic battery tester, and for performing diagnostics on the vehicle.

24. The apparatus of claim 23 includes a memory means for storing information.

25. The apparatus of claim 24 wherein the memory means is for storing information received from the battery tester.

26. The apparatus of claim 23 including means for receiving a user input.

27. The apparatus of claim 23 including means for displaying information.

* * * * *